(12) United States Patent
Vuillermin et al.

(10) Patent No.: US 11,529,380 B2
(45) Date of Patent: Dec. 20, 2022

(54) METHODS AND COMPOSITIONS FOR DETERMINING, AND FOR MINIMIZING, THE LIKELIHOOD OF DEVELOPMENT OF ALLERGY IN INFANTS

(71) Applicant: MURDOCH CHILDREN'S RESEARCH INSTITUTE, Parkville (AU)

(72) Inventors: Peter Vuillermin, Parkville (AU); Anne-Louise Ponsonby, Parkville (AU); Mimi Tang, Parkville (AU)

(73) Assignee: MURDOCH CHILDREN'S RESEARCH INSTITUTE Parkville, Parkville (AU)

(*) Notice: Subject to any disclaimer, the term of this patent is extended or adjusted under 35 U.S.C. 154(b) by 602 days.

(21) Appl. No.: 16/471,058

(22) PCT Filed: Dec. 22, 2017

(86) PCT No.: PCT/AU2017/051453
§ 371 (c)(1),
(2) Date: Jun. 19, 2019

(87) PCT Pub. No.: WO2018/112553
PCT Pub. Date: Jun. 28, 2018

(65) Prior Publication Data
US 2019/0330686 A1 Oct. 31, 2019

(30) Foreign Application Priority Data
Dec. 23, 2016 (AU) ................ 2016905378

(51) Int. Cl.
*A61K 35/741* (2015.01)
*A61B 5/00* (2006.01)
*C12Q 1/689* (2018.01)
*G01N 33/569* (2006.01)

(52) U.S. Cl.
CPC .......... *A61K 35/741* (2013.01); *A61B 5/0004* (2013.01); *C12Q 1/689* (2013.01); *C12Q 2600/118* (2013.01); *C12Q 2600/16* (2013.01); *G01N 33/56916* (2013.01); *G01N 2800/24* (2013.01); *G01N 2800/38* (2013.01); *G01N 2800/50* (2013.01)

(58) Field of Classification Search
CPC .... A61K 35/741; A61B 5/0004; C12Q 1/689; C12Q 2600/118; C12Q 2600/16; C12Q 1/6883; G01N 33/56916; G01N 2800/24; G01N 2800/38; G01N 2800/50; G01N 33/56911; G01N 33/689; A61P 37/08
See application file for complete search history.

(56) References Cited

U.S. PATENT DOCUMENTS

| | | | |
|---|---|---|---|
| 5,789,174 A | 8/1998 | Christian et al. | |
| 5,939,303 A | 8/1999 | Joan et al. | |
| 5,985,605 A | 11/1999 | Joan et al. | |
| 7,943,313 B2 | 5/2011 | Fukui et al. | |
| 8,748,152 B1 | 6/2014 | Hector et al. | |
| 10,137,157 B2 | 11/2018 | Björck et al. | |
| 2015/0174178 A1* | 6/2015 | Kovarik ............... | A61K 35/745 424/282.1 |
| 2016/0074505 A1 | 3/2016 | Kovarik et al. | |
| 2016/0186261 A1 | 6/2016 | Scher et al. | |
| 2016/0224748 A1 | 8/2016 | Apte et al. | |
| 2016/0326574 A1* | 11/2016 | Gordon ................. | C12Q 1/689 |
| 2019/0151376 A1 | 5/2019 | Björck et al. | |

FOREIGN PATENT DOCUMENTS

| | | |
|---|---|---|
| EP | 3016527 | 5/2014 |
| JP | 2002142771 | 5/2002 |
| JP | 2003144199 | 5/2003 |
| JP | 2004057058 | 2/2004 |
| JP | 2007222136 | 9/2007 |
| JP | 2007244349 | 9/2007 |
| RU | 2306341 C1 | 9/2007 |
| RU | 2420589 C1 | 6/2011 |
| WO | WO 1992/021761 | 12/1992 |
| WO | WO 1997/048812 | 12/1997 |
| WO | WO 2001/002008 | 1/2001 |
| WO | WO 2010/129287 | 11/2010 |
| WO | WO 2013/182038 | 12/2013 |
| WO | WO 2014/080991 | 5/2014 |
| WO | WO 2016/112252 | 1/2016 |
| WO | WO 2016/122889 | 8/2016 |
| WO | WO 2016/183535 | 11/2016 |

OTHER PUBLICATIONS

Brook, "Prevotella and Porphyromonas Infections in Children", Clinal Microbiology, 42:340-347, (Year: 1995).*
Edermaniger, Leanne. "Prevotella Bacteria in Gut, Mouth, and Vaginal Microbiome Health", https://atlasbiomed.com/blog/prevotella-bacteria-guide-for-health/, p. 1-13, September (Year: 2006).*
Landhuis"Gut Microbes May Be Key to Solving Food Allergies", https://www.scientificamerican.com/article/gut-microbes-may-be-key-to-solving-food-allergies/, 1-11, May 23, (Year: 2020).*
Extended European Search Report issued in corresponding European Application No. 17882621.0, dated Sep. 25, 2020.
Vuillermin et al., "Abstract No. 1419: Maternal carriage of prevotella during pregnancy is associated with decreased food allergy in the offspring," European Academy of Allergy and Clinical Immunology Congress 2017 (Jun. 17-21, 2017), presented on Jun. 19, 2017, *Allergy*, 72:128, 2017.
Ponsonby et al., "Which clinical subgrouns within the spectrum of child asthma are attributable to atopy?" *Chest*, 121: 135-142, 2002.

(Continued)

*Primary Examiner* — Cynthia B Wilder
(74) *Attorney, Agent, or Firm* — ParkerHighlander, PLLC

(57) ABSTRACT

The invention relates to allergic disease, to the development of allergic disease in infants, to determining the likelihood of development of allergic disease in infants and to minimizing the likelihood of development of allergic disease in infants.

9 Claims, 12 Drawing Sheets
Specification includes a Sequence Listing.

(56) References Cited

OTHER PUBLICATIONS

Tan et al., "Dietary fiber and bacteria SCFA enhance oral tolerance and protect against food allergy through diverse cellular pathways," *Cell Reports*, 15: 2809-2824, 2016.

Thorburn et al., "Evidence that asthma is a developmental origin disease influenced by maternal diet and bacterial metabolites," *Nature Communications*, 6:7320 (1-13), 2015.

Trompette et al., "Gut Microbiota Metabolism of Dietary Fiber Influences Allergic Airway Disease and Hematopoiesis," *Nature Medicine*, Feb;20(2):159-66, 2014.

Vuillermin et al., "Microbial Exposure, Interferon Gamma Gene Demethylation in Naïve T-cells, and the Risk of Allergic Disease," *Allergy*, 64: 348-353, 2009.

GenBank Accession HM805802, "Uncultured bacterium clone C051bD02 16S ribosomal RNA gene, partial Sequence," Jan. 5, 2012.

Gray et al., "The Maternal Diet, Gut Bacteria, and Bacterial Metabolites during Pregnancy Influence Offspring Asthma," *Frontiers in Immunology*, 8:365, 2017.

Lepage et al., "Twin study indicates loss of interaction between microbiota and mucosa of patients with ulcerative colitis," *Gastroenterology*, 141(1):227-36, 2011.

PCT International Search Report and Written Opinion issued in International Application No. PCT/AU2017/051453, dated Feb. 2, 2018.

Vuillermin et al., "The maternal microbiome during pregnancy and allergic disease in the offspring," *Seminars in Immunopathology*, 39(6):669-675, 2017.

\* cited by examiner

Figure 1

*Prevotella copri* strain JCM 13464 16S ribosomal RNA gene, partial sequence
Sequence ID: NR_113411.1  Length: 1493  Number of Matches: 1

Range 1: 529 to 781 GenBank Graphics          Next Match  Previous Match

| Score | Expect | Identities | Gaps | Strand |
|---|---|---|---|---|
| 487 bits(253) | 1e-137 | 253/253(100%) | 0/253(0%) | Plus/Plus |

```
Query  1    TACGGAAGGTCCGGGCGTTATCCGGATTTATTGGGTTTAAAGGGAGCGTAGGCGGAAT    60
            |||||||||||||||||||||||||||||||||||||||||||||||||||||||||||
Sbjct  529  TACGGAAGGTCCGGGCGTTATCCGGATTTATTGGGTTTAAAGGGAGCGTAGGCGGAAT    588

Query  61   TAAGGTGTTGTGAAATGTAGACGCTCAACGTCTGACTTGCAGCGTGAACTGGTTCCTT    120
            |||||||||||||||||||||||||||||||||||||||||||||||||||||||||||
Sbjct  589  TAAGGTGTTGTGAAATGTAGACGCTCAACGTCTGACTTGCAGCGTGAACTGGTTCCTT    648

Query  121  GAGTAGGCACACAAGTGGTGGAATTCGTGGTGTAGCGGTGAAATGCTTAGATATCACGA    180
            |||||||||||||||||||||||||||||||||||||||||||||||||||||||||||
Sbjct  649  GAGTAGGCACACAAGTGGTGGAATTCGTGGTGTAGCGGTGAAATGCTTAGATATCACGA    708

Query  181  GAACTCCGATTGCGAAGGCAGCTCACTGGAGTGCAACTGACGCTGAAGCTCGAAAGTGC    240
            |||||||||||||||||||||||||||||||||||||||||||||||||||||||||||
Sbjct  709  GAACTCCGATTGCGAAGGCAGCTCACTGGAGTGCAACTGACGCTGAAGCTCGAAAGTGC    768

Query  241  GGTATCCAACAGG    253
            |||||||||||||
Sbjct  769  GGTATCCAACAGG    781
```

METHODS AND COMPOSITIONS FOR DETERMINING, AND FOR MINIMIZING, THE LIKELIHOOD OF DEVELOPMENT OF ALLERGY IN INFANTS

This application is a national phase application under 35 U.S.C. § 371 of International Application No. PCT/AU2017/051453, filed Dec. 22, 2017, which claims the benefit of Australian Patent Application No. 2016905378, filed Dec. 23, 2016, the entirety of each referenced disclosure is incorporated herein by reference.

Pursuant to 37 C.F.R. 1.821(c), a sequence listing is submitted herewith as an ASCII compliant text file named "FPAPP0009US ST25.txt", created on Jun. 18, 2019 and having a size of ~18 kilobytes. The content of the aforementioned file is hereby incorporated by reference in its entirety.

TECHNICAL FIELD OF THE INVENTION

The invention relates to allergic disease, to the development of allergic disease in infants, to determining the likelihood of development of allergic disease in infants and to minimizing the likelihood of development of allergic disease in infants.

BACKGROUND OF THE INVENTION

Approximately 30% to 40% of the world's population is affected by allergic disease and the prevalence is increasing. In Australia, for example, there has been a 3-fold increase in emergency department presentations due to food allergy anaphylaxis since the late 1990s, mostly explained by an increase among young children.

Evidence suggests that allergic disease may be associated with diet-induced changes in the gut microbiome. Microbiota-accessible carbohydrates (MACs), found in plant derived dietary fiber, have been proposed to play a role in shaping the gut microbial ecosystem, which, in turn, is believed to influence immune regulation. The gut microbiota of hunter-gatherers that consume a high MAC diet contains greater bacterial species diversity than the gut microbiota of Westerners. In particular, hunter-gatherers have a substantially greater abundance of anaerobic organisms, mostly of the phyla Bacteroidetes, and in particular the genus *Prevotella*. These anaerobic organisms have been proposed to play a role in liberating energy from dietary MACs via fermentation resulting in the production of metabolites including short chain fatty acids (SCFAs). SCFAs, in turn, are thought to increase microbial diversity, dampen inflammatory pathways, and promote the development of regulatory T cells (Treg) that are required to maintain tolerance to self and non-self antigens.

The majority of microbiome-immune research has focused on the postnatal period. There is however, evidence from mouse models that maternal dietary MAC intake during pregnancy induces changes in the maternal gut microbiome. In turn, maternal transfer of metabolites, including SCFAs, is thought to influence foetal immune programming and the development of postnatal allergic disease.

There remains a need to develop intervention strategies for minimizing the likelihood of development of allergic disease in infants and children.

It will be understood that although a number of prior art publications are referred to herein such reference does not constitute an admission that any of these documents forms part of the common general knowledge in the art in any country.

SUMMARY OF THE INVENTION

The invention in a first aspect provides a method of determining whether an offspring of a pregnant mother is susceptible to developing an allergic disease, the method comprising detecting the level of bacteria of *Prevotella* 9 in a faecal sample from the pregnant mother, wherein the absence of detectable *Prevotella* 9 or the presence of low levels of *Prevotella* 9 indicates that the offspring is susceptible to developing an allergic disease.

A second aspect provides use of the method of the first aspect to determine whether a pregnant mother should be treated to increase the level of bacteria of *Prevotella* 9 in their gut to reduce the susceptibility of their offspring to developing an allergic disease.

A third aspect provides the use of the method of the first aspect to determine whether a pregnant mother has been effectively treated to increase the level of bacteria of *Prevotella* 9 in their gut.

A fourth aspect provides a method of preventing allergic disease in an infant, the method comprising maintaining *Prevotella* 9 levels in the infant's mother when pregnant at a level of abundance that is (a) detectable, and (b) at higher levels of abundance.

The method of the fourth aspect may involve administering to the infant's mother a therapeutically effective amount of microbiota accessible carbohydrates, for example in the subject's diet. The method may also comprises administering to the infant's mother a therapeutically effective amount of a bacteria of the genus *Prevotella* 9.

In an embodiment of each of the first to fourth aspects the allergic disease is allergic rhinitis, IgE-mediated food allergy, atopic dermatitis, atopic wheeze and asthma.

A fifth aspect provides a kit for determining the level of bacteria of *Prevotella* 9 in a sample, the kit comprising primers specific for *Prevotella* 9

The primers may be specific for *Prevotella* 9×16S ribosomal nucleic acid region of SEQ ID NO: 1:

```
                                               (SEQ ID NO: 1)
TACGGAAGGTCCGGGCGTTATCCGGATTTATTGGGTTTAAAGGGAGCGTA

GGCCGGAGATTAAGCGTGTTGTGAAATGTAGACGCTCAACGTCTGCACTG

CAGCGCGAACTGGTTTCCTTGAGTACGCACAAAGTGGGCGGAATTCGTGG

TGTAGCGGTGAAATGCTTAGATATCACGAAGAACTCCGATTGCGAAGGCA

GCTCACTGGAGCGCAACTGACGCTGAAGCTCGAAAGTGCGGGTATCGAAC

AGG
```

In one embodiment the primers comprise:

```
OTU_41 For
                                               (SEQ ID NO: 3)
TACGGAAGGTCCGGGCGTTAT

OTU41_Rev
                                               (SEQ ID NO: 4)
AGTGCAGACGTTGAGCGTCTA
```

The primers may be specific for target *Prevotella* 9 species Y 16S ribosomal nucleic acid region of SEQ ID NO: 2:

(SEQ ID NO: 2)
TACGTATGGTGCAAGCGTTATCCGGATTTATTGGGTTTAAAGGGAGCGTA

GGCCGGAGATTAAGCGTGTTGTGAAATGTAGATGCTCAACATCTGAACTG

CAGCGCGAACTGGTTTCCTTGAGTACGCACAAAGTGGGCGGAATTCGTGG

TGTAGCGGTGAAATGCTTAGATATCACGAAGAACTCCGATTGCGAAGGCA

GCTCACTGGAGCGCAACTGACGCTGAAGCTCGAAAGTGCGGGTATCGAAC

AGG

In one embodiment the primers comprise:

OTU_697 For
(SEQ ID NO: 5)
TACGTATGGTGCAAGCGTT

OTU_697 Rev
(SEQ ID NO: 6)
GCAGTTCAGATGTTGAGCATC

Another aspect provides a method for minimizing the likelihood of development of allergy in offspring or progeny of a female individual comprising the step of administering *Prevotella* to the female individual thereby minimizing the likelihood of development of allergy in progeny of the female individual.

Another aspect provides a *Prevotella* for use by administration to a female individual in minimizing the likelihood of development of allergy in progeny of the female individual.

Another aspect provides a use of *Prevotella* in a female individual to minimize the likelihood of development of allergy in progeny of the female individual.

Another aspect provides a composition formulated for human consumption comprising, or consisting of bacteria that is *Prevotella*.

Another aspect provides a composition formulated for human consumption comprising, or consisting of:
  bacteria having a 16S rDNA sequence shown in SEQ ID NO: 1; or
  bacteria having a 16S rDNA sequence having at least 97% identity, preferably 98% identity, preferably 99% identity with the sequence shown in SEQ ID NO: 1 or
  bacteria having a 16S rDNA sequence shown in SEQ ID NO: 2; or
  bacteria having a 16S rDNA sequence having at least 97% identity, preferably 98% identity, preferably 99% identity with the sequence shown in SEQ ID NO: 2.

Another aspect provides a composition comprising: *Prevotella copri*, and a further ingredient that is beneficial for a pregnant or lactating woman.

Another aspect provides a use of *Prevotella* in the manufacture of a composition for administration to a female individual to minimize the likelihood of development of allergy in progeny of the female individual.

Further aspects and embodiments of the invention described in the preceding paragraphs will become apparent from the following description, given by way of example and with reference to the accompanying figures.

BRIEF DESCRIPTION OF DRAWINGS

FIG. 1 shows The National Centre for Biotechnology Information BLAST similarity search for OTU000041 in the 16S ribosomal RNA sequences (Bacteria and Archacea) indicates 100% homology with the species *Prevotella copri* strain 13464.

FIG. 2 shows the region of homology is in the V4 section of the gene (OTU000041 underlined).

DETAILED DESCRIPTION OF THE INVENTION

Standard Methods

Figure 3:
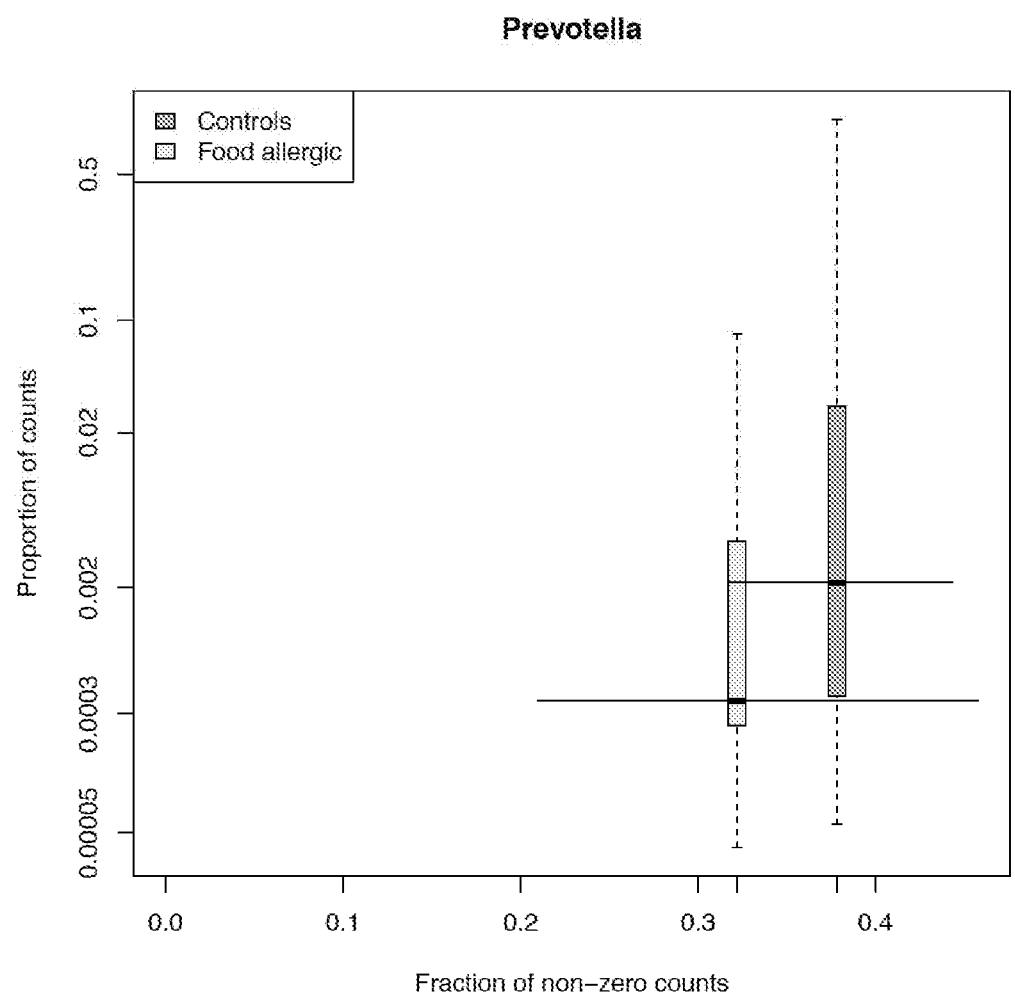
FIG. 3 shows the distribution of the relative abundance of OTUs corresponding to the *Prevotella* genus among stool samples collected during pregnancy from mothers of infants with subsequent food allergy versus mothers of infants without food allergy.

Unless specifically defined otherwise, all technical and scientific terms used herein shall be taken to have the same meaning as commonly understood by one of ordinary skill in the art (e.g., in microbiology, biochemistry, and immunology).

Unless otherwise indicated, the microbiology, biochemistry, and immunological techniques utilized in the present invention are standard procedures, well known to those skilled in the art. Such techniques are described and explained throughout the literature in sources such as, J, Perbal, A Practical Guide to Molecular Cloning, John Wiley and Sons (1984), J. Sambrook and Russell., Molecular Cloning: A Laboratory Manual, 3rd edn, Cold Spring Harbour Laboratory Press (2001), R. Scopes, Protein Purification—Principals and Practice, 3rd edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Definitions

In the present invention, the term "allergic disease" is a general term for diseases in which allergic reaction is involved. More specifically, a disease which is an allergic disease is one associated with allergic sensitization. 'Allergic sensitization' refers to the production of significant levels of allergen-specific IgE antibodies. Allergic sensitization can be identified by skin prick allergy testing or by measurement of serum allergen-specific IgE levels. Examples of allergens include food allergen, mite allergen, pollen allergen. Representative allergic diseases include bronchial asthma, atopic wheeze, allergic rhinitis, atopic dermatitis, pollen allergy, food allergy, insect allergy, and such. Familial allergic diseases may also be called atopic diseases.

"Allergen" as used herein refers to any naturally occurring protein or mixtures of proteins that may induce allergic reactions (i.e. IgE-mediated reactions, or allergic sensitization). Examples of naturally occurring allergens include pollen allergens (tree, weed, herb and grass pollen allergens), mite allergens (from house dust mites and storage mites), insect allergens (inhalant, saliva and venom origin allergens), animal allergens (from saliva, hair and dander from dog, cat, horse, rat, mouse), fungi allergens and food allergens.

"Food allergy" as used herein refers to allergic sensitization and to IgE-mediated reaction to food allergens. Food sensitization may be detected by a positive skin prick test (SPT) to a food allergen which may include cow's milk, egg, peanut, sesame or cashew. A positive SPT may be a wheal diameter at least 2 mm greater than that produced by a negative control solution, measured at 15 minutes. Food sensitization may also be detected by the presence of elevated levels of allergen specific IgE in serum.

"Atopic wheeze" as used herein refers to the presence of parent-reported wheeze during the first year of life associated with allergic sensitization. Atopic wheeze may be assessed by SPT wherein a positive SPT result and wheeze indicates atopic wheeze. The SPT may measure sensitization to any of the food antigens or other allergens or aeroallergens herein.

"Atopic eczema" as used herein refers to the presence of eczema as defined according to the Modified UK working party criteria for infants under 12 months (Williams, Burney et al. 1994, Fleming, Bodner et al. 2001). Atopic eczema may be assessed by SPT wherein a positive SPT result and eczema indicates atopic eczema. The SPT may measure sensitization to any of the food antigens or other allergens or aeroallergens herein.

"Microbiota" as used herein refers to one or more bacterial communities that can be found or can exist (colonize) within a gastrointestinal tract of a host organism, also described herein as "gut microbes".

"Operational taxonomic units" (OTUs) as used herein refers to groups of organisms grouped by DNA sequence similarity.

"Microbiota-accessible carbohydrates" (MACs) as used herein refers to carbohydrates that are resistant to digestion by a host's metabolism, and are made available for gut microbes, as prebiotics, to consume or ferment or metabolize or convert into beneficial compounds or substances or metabolites, such as short chain fatty acids. Microbiota accessible carbohydrates as used herein are particularly found in "high fiber" diets and have the effect of increasing the level of certain species of bacteria in the gut.

"Prebiotic" as used herein refers to any substance that can be consumed by a relevant bacteria, or that otherwise assists in keeping the relevant bacteria alive or stimulates its growth.

"Short chain fatty acids" as used herein refers to fatty acids with fewer than six carbon atoms and include, but are not limited to, acetate, butyrate and propionate.

"Gut" as used herein refers to the digestive tract, in particular the intestine and stomach. An "increase in the gut" as used herein refers to an increase in the level of bacteria present in a feacal sample, as being indicative of gut levels.

"Offspring" as used herein refers to one or more immediate children or young or progeny of a particular pregnant female from a single pregnancy.

A "subject" as used herein may be human or a non-human animal, for example a domestic, a zoo, or a companion animal. In one embodiment, the subject is a mammal. The mammal may be an ungulate and/or may be equine, bovine, ovine, canine, or feline, for example. Accordingly, the present invention has human medical application, and also veterinary and animal husbandry applications, including treatment of domestic animals such as horses, cattle and sheep, and companion animals such as dogs and cats.

An infant subject is a subject less than 1 year of age.

"*Prevotella*" as used herein refers to a genus of gram negative anaerobic bacteria of the phylum Bacteroidetes. OTUs 41 and 697 as having the best support (p-values adjusted for multiple testing 0.003 and 0.009 respectively; next lowest p-value 0.19) were classified as *Prevotella_9*, a subgroup of *Prevotella* containing two described species, *Prevotella copri* and *P. paludivivens*. *Prevotella* 9 species X as used herein refers to a strain of *Prevotella* identifiable by 97% sequence identity to operational taxonomic unit (OTU) 000041 at the V4 16S rDNA locus, which in turn has 100% sequence identity to *Prevotella copri*. *Prevotella* 9 species Y as used herein refers to a *Prevotella* species identifiable by 97% sequence identity to OTU 000697 at the V4 16S rDNA locus. This has 98% similarity to *P. copri* but is likely a separate strain or species within *Prevotella*. *Prevotella* species X and *Prevotella* species Y are both classified into the *Prevotella* 9 subgroup.

A composition "conditioned by" *Prevotella* as used herein refers to composition that comprises secretions of *Prevotella*. The composition is preferably acellular. Such a composition may be the supernatant of a culture of *Prevotella* from which bacterial cells and fragments have been removed.

A composition of the invention that is "formulated for human consumption" as used herein refers to a composition that (a) contains excipients, diluents or carriers that are generally regarded as safe for consumption by humans and/or (b) does not contain ingredients or components that are unsafe for human consumption.

Throughout the description and claims of this specification, the word "comprise" and variations of the word, such as "comprising" and "comprises", means "including but not limited to", and is not intended to exclude other additives, components integers or steps.

"Nucleic acid" as used herein refers to DNA molecules cDNA or genomic DNA), RNA molecules (e.g. mRNA), DNA-RNA hybrids, and analogs or the DNA or RNA generated using nucleotide analogs. The nucleic acid molecule can be a nucleotide, oligonucleotide, double-stranded DIVA, single-stranded DNA, multi-stranded DNA, complementary DNA, genomic DNA, non-coding DNA, messenger RNA (mRNA), microRNA (miRNA), small nucleolar RNA (snoRNA), ribosomal RNA (rRNA), transfer RNA (tRNA), small interfering RNA (siRNA), heterogeneous nuclear RNAs (hnRNA), or small hairpin RNA (snRNA).

The term "therapeutically effective amount" refers to an amount of microbiota accessible carbohydrate or bacteria of *Prevotella* 9 capable of treating allergic disease in a subject or preventing allergic disease in the offspring of a subject receiving the treatment.

The terms "treat", "treating" or "treatment" refer to both therapeutic treatment and prophylactic or preventative measures, wherein the aim is to prevent or ameliorate allergic disease in an infant subject or slow down (lessen) progression of allergic disease in an infant subject. Infant subjects in need of treatment include those already with the allergic disease as well as those in which development of the allergic disease is to be prevented by treatment of the mother in pregnancy or the infant.

"Conditioning" with respect to the female individual generally refers to bringing the female individual to a desired state in which the likelihood of development of allergic disease in progeny of the female individual is minimized or reduced. This may generally be achieved according to the methods described herein.

As used herein, the phrase "level of bacteria" refers to the number, concentration or amount of bacteria in a sample and the phrase "increasing the level of a bacteria" refers to an increase in the number, concentration or amount of a bacterium or bacterial DNA in the sample as a result of treatment as described herein, and when compared to a subject who has not been treated according to the method described herein.

As used herein the "level of bacteria" is a "marker" or "biomarker" indicative or predictive of allergic disease. A "marker" or "biomarker" refers to a biochemical, genetic, metabolic or molecular characteristic or substance or metabolite that is indicative or predictive of allergic disease. As such, the "level of a biomarker or marker" may be indicative of the "level of bacteria".

A level of bacteria in a sample below a "reference level", as used herein, predictive of allergic disease. For *Prevotella* 9 species X, the "reference level" of bacteria is the presence of detectable DNA specific to species X in the faecal sample. For *Prevotella* 9 species Y, the "reference level" of bacteria is the presence of detectable DNA specific to species Y in the faecal sample. Our data further indicate that among mothers with detectable *Prevotella* 9 species X and/or *Prevotella* 9 species Y a relative abundance of this DID relative to the total OTU count in the sample greater than 0.0003 is associated with a greater decrease in offspring allergic disease.

As used herein, "determining whether an offspring of a pregnant mother is susceptible to developing an allergic disease" "refers to detecting or diagnosing allergic disease in an infant subject, or predicting or prognosing, that an infant subject is likely to develop allergic disease by assaying the infant's mother during pregnancy. The invention also encompasses detecting susceptibility to allergic disease in an infant subject. "Susceptible" as used herein is defined as detecting a level of bacteria of the genus *Prevotella* 9 species X and/or Y below the reference level. Further that detectable but low abundance of *Prevotella* 9 species X and/or Y is associated with greater offspring allergic disease than greater abundance of detectable *Prevotella* species X and/or Y.

"Maintaining *Prevotella* 9 species X and/or Y levels in the infant's mother when pregnant at above reference level" as used herein refers to maintaining *Prevotella* 9 species X levels within a detectable range in a faecal sample from the mother, and maintaining *Prevotella* 9 species Y levels within a detectable range. Further, that maintaining higher levels of *Prevotella* species X and/or Y levels in the infant's mother when pregnant is associated with a greater decrease in offspring allergic disease.

Repeated testing could be used to encourage optimization of (a) the level of bacteria of *Prevotella* 9 present during pregnancy, and (b) the duration of pregnancy during which *Prevotella* 9 species are present during pregnancy.

A. Determining Likelihood of Development of Allergic Disease in Infants

The invention in a first aspect provides a method of determining whether an offspring of a pregnant mother is susceptible to developing an allergic disease, the method comprising detecting the level of bacteria of *Prevotella* 9 in a faecal sample from the pregnant mother, wherein the absence of detectable *Prevotella* 9 or the presence of low levels of *Prevotella* 9 indicates that the offspring is susceptible to developing an allergic disease.

The invention provides a method for determining the likelihood of a female individual forming offspring having allergic disease. The method comprises the following steps:
  providing a control describing the relative abundance of *Prevotella* 16S rDNA in the stool of a mother who has offspring who do not have allergic disease;
  obtaining a sample from the female individual for whom the likelihood of forming offspring having allergic disease is to be determined, thereby forming a test sample;
  comparing the test sample with the control to assess whether the test sample has a relative abundance of *Prevotella* 16S rDNA as described in the control;
  determining that the female individual has a low likelihood of forming offspring having allergic disease where the test sample has a relative abundance of *Prevotella* 16S rDNA as described in the control
  determining that the female individual has a high likelihood of forming offspring having allergic disease where the test sample has a relative abundance of *Prevotella* 16S rDNA that is not described in the control.

A female individual having a lower relative abundance of a *Prevotella* 16S rDNA, especially of OTU00041 or SEQ ID NO: 1 than the control has a higher likelihood of forming offspring having allergic disease.

A female individual having no OTU000697 or SEQ ID NO: 2, or lower relative abundance of OTU000697 or SEQ ID NO: 2 than the control, has a higher likelihood of forming offspring having allergic disease.

The control may be derived from one mother, preferably from a cohort of mothers, at least about 10, 20, 50 or 100 mothers.

The control may be in the form of a data file, or in the form of a biological sample.

The control or test sample may be based on assessment of a stool sample, or on the basis of a biological sample from which the amount of 16S rDNA in the stool can be determined. Preferably the test sample is based on assessment of a stool.

The relative abundance of 16S rDNA may be determined by any of the techniques described below under this subheading. The technique may measure the amount of 16S rDNA directly, or indirectly by measuring some other parameter, for example cfu of *Prevotella* isolated from a sample.

The method may comprise the assessment of relative abundance of 16S ribosomal nucleic acid of *Prevotella*_9, or *Prevotella*_9 species X, or *Prevotella*_9 species Y, or OTU00041 or OTU00697, or of SEQ ID NO: 1 or of SEQ ID NO: 2.

The control may describe the relative abundance of OTU00041 or SEQ ID NO: 1, or OTU000697 or SEQ ID NO: 2. The test sample may be assessed to determine relative abundance of OTU00041 or SEQ ID NO: 1, or OTU000697 or SEQ ID NO: 2.

The method may utilize an oligonucleotide having a sequence shown in SEQ ID NO: 3, 4, 5 or 6.

The female individual for whom the likelihood of forming offspring having allergic disease is to be determined may be pregnant, or planning pregnancy. Preferably the female individual is pregnant.

Methods for determining the level or amount of bacteria in a sample are known to those skilled in the art. The presence of bacteria may be identified using microbiological culture techniques, biochemical assays or molecular techniques including, but not limited to, PCR (polymerase chain reaction), nucleic acid hybridisation or sequencing techniques. Alternatively, the method may comprise amplifying a bacterial nucleic acid sequence by a technique such as PCR and cloning and/or sequencing the nucleic acid. Identification of bacteria may also be achieved by sequencing of 16S rDNA, including the use of next-generation high-throughput sequencing technologies.

Bacteria may also be detected using immunological methods. For example, antisera or antibodies cross reactive with a bacteria of the genus *Prevotella* 9 species X and/or Y may be used in a suitable immunological assay. Immunogical assays include enzyme-linked immunosorbent assay (ELISA), and those that use solid supports such as dip-stick type assays. Such immunological assays may utilise labelled antibodies, including fluorescent, radioactive or chemiluminescent labelled antibodies or dye molecules.

Any suitable technique that allows for the qualitative and/or quantitative detection of a nucleic acid from a bacteria of the genus *Prevotella* 9 species X and/or Y may be used. Comparison may be made by reference to a standard control, or to a negative control. The nucleic acid may be labelled and hybridised on a gene array, in which case the gene concentration will be directly proportional to the intensity of the radioactive or fluorescent signal generated in the array.

In certain embodiments of the present invention, ribosomal nucleic acid can be used to distinguish and detect bacteria. For example, bacterial ribosomes are comprised of a small and large subunit, each which is further comprised of ribosomal nucleic acid and proteins. A large number of ribosomal nucleic acids have been sequenced, and these are publicly available in various accessible databases. Thus, in one embodiment, bacteria of the genus *Prevotella* 9 species X and/or Y is detected in a sample by sequencing 16S ribosomal nucleic acid amplicons generated by domain-level PCR reactions amplifying from genomic DNA. Traditionally, sequencing of ribosomal nucleic acids was performed by cloning and Sanger (capillary electrophoresis) sequencing of PCR amplicons. The advent of next-generation sequencing has simplified and increased the sequencing depth for 16S ribosomal nucleic acid sequencing.

Accordingly, a "nucleic-acid-based detection assay" as used herein, is an assay for the detection of a target sequence within a target nucleic acid and utilizing one more oligonucleotides that specifically hybridize to the target sequence.

B. Minimizing the Likelihood of Development of Allergic Disease

A fourth aspect provides a method of preventing allergic disease in an infant, the method comprising maintaining *Prevotella* 9 levels in the infant's mother when pregnant at a level of abundance that is (a) detectable, and (b) at higher levels of abundance.

The invention provides a method for conditioning a female individual to minimize the likelihood of development of allergy in offspring or progeny of the female individual. It will be understood that the administration of *Prevotella* to the female individual is for the purpose of conditioning the female individual, or in other words, for the purpose of preparing the female so as to minimize the likelihood that the female might form offspring or progeny having allergy. Relevantly, the administration of *Prevotella* is not a therapeutic use of *Prevotella* because it is not for the purpose of treating a disease or condition or ailment of the female.

The invention provides a method for minimizing the likelihood of development of allergy in offspring or progeny of a female individual.

The methods of the invention comprise the step of administering *Prevotella* to the female individual. The administration of *Prevotella* to the female individual is to minimize the likelihood of development of allergy in progeny of the female individual. As exemplified herein, the absence of maternal carriage of *Prevotella* is strongly associated with a higher likelihood of development of allergic disease in offspring. It follows that this risk factor is minimised by the administration of *Prevotella* to the female individual.

The invention provides *Prevotella* for use by administration to a female individual in minimizing the likelihood of development of allergy in progeny of the female individual.

The invention provides a use of *Prevotella* in a female individual to minimize the likelihood of development of allergy in progeny of the female individual.

The female individual may be an individual who has been assessed to determine the likelihood of development of allergic disease in her progeny including according to a method under the previous subheading. On the basis of the assessment, the female individual is administered *Prevotella*. The female individual may be administered *Prevotella* irrespective of the assessment outcome.

Where the female individual is assessed to determine her likelihood of forming progeny having allergy, it is preferred that the assessment is a consideration of her carriage of *Prevotella*. The assessment may be to determine whether the female individual has an absence of detectable *Prevotella* in her gut. Alternatively, the assessment may be to determine the relative abundance of *Prevotella* in her gut. Preferably the assessment is to determine whether the female individual has an absence of detectable *Prevotella* in her gut. The assessment may be on the basis of detection of *Prevotella* specific polynucleotide sequences in her gut or faeces, for example utilizing nucleic acid detection techniques described herein. In other embodiments, the assessment of the risk factor may be generally on the basis of a consideration discussed above.

In another embodiment, the female individual to whom the method is applied has not been assessed to determine the likelihood of forming progeny having allergic disease. According to this embodiment, the female individual is unaware of her risk profile for forming progeny having allergic disease. According to the embodiment, the female individual is administered *Prevotella* simply to minimize the risk that would apply should she have a high likelihood of forming progeny having allergic disease.

The female individual may be a prospective mother (i.e. a female who is yet to fall pregnant and who intends to do so) or an expectant mother (i.e. a pregnant female).

In one embodiment, the female individual is an expectant mother i.e. pregnant when the first administration of *Prevotella* is given to the female individual.

In another embodiment, the female individual is not pregnant (i.e. may be a prospective mother) at the time of first administration of *Prevotella*. For example, *Prevotella* may be given to a prospective mother 1 to 3 months, preferably no more than about 6 months to a prospective mother prior to her falling pregnant. In this embodiment, *Prevotella* may also be administered to the female individual during pregnancy.

The *Prevotella* may be administered in the $1^{st}$, $2^{nd}$ or $3^{rd}$ trimester, or in all trimesters. In one embodiment, the *Prevotella* is administered in the $3^{rd}$ trimester only. In one embodiment, the *Prevotella* is administered in the $2^{nd}$ trimester only. In one embodiment, the *Prevotella* is administered in the $2^{nd}$ and $3^{rd}$ trimester only. In one embodiment, the *Prevotella* is administered for at least 2 months, more preferably for at least 4 months before delivery. Thus the female individual may receive *Prevotella* for part or all of her pregnancy.

In one embodiment, the female individual herself may be at risk of atopic disease. For example, a prospective mother, or expectant mother may have atopic sensitization and either a history of allergic disease or active allergic disease. Examples include atopic eczema, allergic rhinoconjunctivitis, food allergy or asthma. As mentioned above, the administration of *Prevotella* is not for the purpose of treating a disease or condition or ailment of the female.

In the above described embodiments, the *Prevotella* that is administered to the female individual may comprise, or may consist of *Prevotella* 9. The *Prevotella* that is administered to the female individual may comprise, or may consist of *Prevotella_9* species X. The *Prevotella* that is administered to the female individual may comprise, or may consist of *Prevotella_9* species Y. The *Prevotella* that is administered to the female individual may comprise, or may consist of *Prevotella copri*. The *Prevotella* that is administered to the female individual may comprise, or may consist of bacteria having a 16S rDNA sequence shown in SEQ ID NO: 1; or bacteria having a 16S rDNA sequence having at least 97% identity, preferably 98% identity, preferably 99% identity with the sequence shown in SEQ ID NO: 1 or bacteria having a 16S rDNA sequence shown in SEQ ID NO: 2; or bacteria having a 16S rDNA sequence having at least 97% identity, preferably 98% identity, preferably 99% identity with the sequence shown in SEQ ID NO: 2.

In the above described embodiments, the female individual may be administered with *Prevotella* to provide from $1 \times 10^6$ to $1 \times 10^{11}$ colony forming units (cfu) of *Prevotella* per day to the female individual.

The *Prevotella* may be administered once or twice daily, for example at meal times, or once every 2 or 3 days, or once weekly.

In the above described embodiments, the *Prevotella* may be provided in the form of a composition. Compositions are described under the following sub-heading.

Typically, *Prevotella* is provided orally to the female individual in the form of a capsule, tablet or like formulation adapted for oral administration. In another embodiment the *Prevotella* may be provided in the form of a food or beverage. *Prevotella* can be administered to the prospective or expectant mother in a variety of ways as long as it there is contact between the *Prevotella* and the gastro-intestinal tract of the mother, preferably with about $10^7$ to $10^{11}$ bacteria.

The invention provides a method for conditioning a pregnant female to minimize the likelihood of her forming progeny that will develop allergic disease, or otherwise, to minimize the likelihood of development of allergy in progeny of the pregnant female, comprising orally administering a composition comprising *Prevotella copri*, to the pregnant female, wherein the administration provides the pregnant female with about $10^6$ to $10^{11}$ cfu per day throughout the $3^{rd}$ trimester, thereby minimizing the likelihood of her forming progeny that will develop allergic disease.

The invention provides a composition comprising *Prevotella copri* for use by oral administration to a pregnant female to provide the pregnant female with about $10^6$ to $10^{11}$ cfu per day throughout the $3^{rd}$ trimester, in minimizing the likelihood of development of allergy in progeny of the female individual.

The invention provides a use of *Prevotella copri* in the manufacture of a composition for oral administration to a pregnant female to provide the pregnant female with about $10^6$ to $10^{11}$ cfu per day throughout the $3^{rd}$ trimester, to minimize the likelihood of development of allergy in progeny of the female individual.

C. Compositions

The invention provides a composition formulated for human consumption. Typically the composition does not comprise supernatant from *Prevotella* culture, or components of culture media for culture of *Prevotella*, other than water. The composition may be used in an above described method to minimize the likelihood of development of allergy in offspring. In one embodiment, the composition formulated for human consumption may comprise, or consist of bacteria that is *Prevotella*. The composition formulated for human consumption may comprise, or consist of bacteria that is *Prevotella_9*. The composition formulated for human consumption may comprise, or consist of bacteria that is *Prevotella_9* species X. The composition formulated for human consumption may comprise, or consist of bacteria that is *Prevotella_9* species Y. The composition formulated for human consumption may comprise, or consist of bacteria that is *Prevotella copri*. In the aforementioned embodiments, the composition may further include a further ingredient selected from the group consisting of a vitamin, a mineral, a long chain polyunsaturated fatty acid, a non digestible oligosaccharide, or a protein, fat or digestible carbohydrate.

In another embodiment there is provided a composition formulated for human consumption. Typically the composition does not comprise supernatant from bacterial culture, or components of culture media for culture of bacteria, other than water. The composition may be used in an above described method to minimize the likelihood of development of allergy in offspring. In one embodiment, the composition formulated for human consumption may comprise, or consist of, bacteria selected from the group consisting of: bacteria having a 16S rDNA sequence shown in SEQ ID No: 1; or bacteria having a 16S rDNA sequence having at least 97% identity, preferably 98% identity, preferably 99% identity with the sequence shown in SEQ ID NO: 1 or bacteria having a 16S rDNA sequence shown in SEQ ID NO: 2; or bacteria having a 16S rDNA sequence having at least 97% identity, preferably 98% identity, preferably 99% identity with the sequence shown in SEQ ID NO: 2. In the aforementioned embodiments, SEQ ID NO: 1 or SEQ ID NO: 2 may each form a V4 structure of a ribosomal RNA molecule. In the aforementioned embodiments, the composition may further include a further ingredient selected from the group consisting of a vitamin, a mineral, a long chain polyunsaturated fatty acid, a non-digestible oligosaccharide, or a protein, fat or digestible carbohydrate.

In another embodiment there is provided a composition formulated for human consumption. Typically the composition does not comprise supernatant from *Prevotella* culture, or components of culture media for culture of *Prevotella*, other than water. The composition may be used in an above described method to minimize the likelihood of development of allergy in offspring. In one embodiment, the composition formulated for human consumption may comprise, or consist of, bacteria selected from the group consisting of: bacteria having a 16S rDNA sequence shown in SEQ ID NO: 8; or bacteria having a 16S rDNA sequence having at least 80% identity to the sequence shown in SEQ ID NO: 8, provided that the sequence includes V4 16S rDNA sequence shown in SEQ ID NO: 7; or bacteria having a 16S rDNA sequence shown in SEQ ID NO: 9; or bacteria having a 16S rDNA sequence having at least 80% identity to the sequence shown in SEQ ID NO: 9, provided that the sequence includes V4 16S rDNA sequence shown in SEQ ID NO: 7; or bacteria having a 16S rDNA sequence shown in SEQ ID NO: 10; or bacteria having a 16S rDNA sequence having at least 80% identity to the sequence shown in SEQ ID NO: 10, provided that the sequence includes V4 16S rDNA sequence shown in SEQ ID NO: 7; or bacteria having a 16S rDNA sequence shown in SEQ ID NO: 11; or bacteria having a 16S rDNA sequence having at least 80% identity to the sequence shown in SEQ ID NO: 11, provided that the sequence includes V4 16S rDNA sequence shown in SEQ ID NO: 7; or bacteria having a 16S rDNA sequence shown in SEQ ID NO: 12; or bacteria having a 16S rDNA sequence having at least 80% identity to the sequence shown in SEQ ID NO: 12, provided that the sequence includes V4 16S rDNA sequence shown in SEQ ID NO: 7. In the aforementioned embodiments, bacteria may be a strain having a 16S rDNA sequence having at least 85%, or 90%, or 95%, or 96%, or 97%, or 98%, or 99% identity to the sequence shown in any one of SEQ ID NO: 8, 9, 10, 11, or 12, provided that the sequence includes SEQ ID NO: 7. In the aforementioned embodiments, the composition may further include a further ingredient selected from the group consisting of a vitamin, a mineral, a long chain polyunsaturated fatty acid, a non digestible oligosaccharide, or a protein, fat or digestible carbohydrate.

In another embodiment there is provided a composition formulated for human consumption comprising a strain of *Prevotella copri* that has been isolated from anaerobic culture medium supernatant, the strain having a 16S rDNA sequence having at least 50% identity to the sequence shown in SEQ ID NO: 8 provided that the sequence includes SEQ ID NO: 7.

In the above described compositions, bacteria may be a strain having a 16S rDNA sequence having at least 85%, or 90%, or 95%, or 96%, or 97%, or 98%, or 99% identity to the sequence shown in any one of SEQ ID NO: 8, 9, 10, 11, or 12, provided that the sequence includes SEQ ID NO: 7.

In the above described embodiments, the composition may further include a further ingredient selected from the group consisting of a vitamin, a mineral, a long chain polyunsaturated fatty acid, a non digestible oligosaccharide, or a protein, fat or digestible carbohydrate.

Percent sequence identity may be determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C D., (1970), Journal of Molecular Biology, 48, 443-453, which is hereby incorporated by reference in its entirety. GAP may be used with the following settings for polynucleotide sequence comparison: GAP creation penalty of 5.0 and GAP extension penalty of 0.3.

In another embodiment there is provided a composition formulated for human consumption comprising a strain of bacteria deposited as DSM number 18205 (JCM13464; CB7) with Leibniz Institute DSMZ-German Collection of Microorganisms and Cell Cultures, InhoffenstraSe 7B 38124 Braunschweig GERMANY. The composition may further include a further ingredient selected from the group consisting of a vitamin, a mineral, a long chain polyunsaturated fatty acid, a non digestible oligosaccharide, or a protein, fat or digestible carbohydrate.

In embodiments herein, reference to a bacterial strain specified by DSM number 18205 may be taken to encompass variants thereof having at least 80% identity with the 16S rRNA sequence of said specified strain, preferably at least 85% identity, more preferably at least 90% identity, further preferably at least 95% identity. In a particularly preferred embodiment, said variant has at least 97% identity with the 16S rRNA sequence of said specified strain, more preferably at least 98% identity, more preferably at least 99% identity.

In embodiments herein reference to *Prevotella copri* or DSM number 18205 may be taken to include functionally equivalent bacteria derived therefrom such as but not limited to mutants, variants or genetically transformed bacteria. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or prophylactic interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling".

In one embodiment there is provided a composition comprising:

*Prevotella copri*; and a further ingredient that is beneficial for a pregnant or lactating woman.

The further ingredient may be a micronutrient. The micronutrient may be a vitamin selected from the group consisting of: vitamin B1 (thiamine), vitamin B2 (riboflavin), vitamin B3 (niacin), vitamin B5 (pantothenic acid), vitamin B6 (pyridoxine), folic acid, vitamin B12 (cyanocobalamine), biotin, choline, and vitamin C, vitamin D3, vitamin E and vitamin K.

The micronutrient may be a mineral selected from the group consisting of calcium, phosphorus, zinc, iodine, iron, manganese, selenium, copper, and magnesium.

The micronutrient may be a long chain polyunsaturated fatty acid (LC-PUFA). The LC-PUFA may be selected from fatty acids having fatty acyl chain with a length of 20 carbon atoms or more and at least two unsaturated bonds. The LC-PUFA may be selected from the group consisting of eicosapentaenoic acids and/or acyl chain (EPA), docosahexaenoic acid and/or acyl chain (DHA) and arachidonic acid and/or acyl chain (AA).

The composition may further include a further bacteria species. The further bacteria species may be selected to (i) reduce the likelihood of food allergy in neonates or infants; and/or (ii) reduce likelihood of inflammation of breast tissue. The further bacteria species may be of genus *Lactobacillus* or *Bifidobacterium*. The further bacteria species may be selected from the group consisting of the *Lactobacillus accidophilus* group, *L. rhamnosus*, *L. casei*, *L. paracasei*, *L. plantarum*, *L. reuteri*, *L. fermentum*, *Bifidobacterium infantis*, *B. animalis* subsp. *lactis*, *B. breve*, *B. longum* and *B. bifidum*.

The composition may further include a non-digestible oligosaccharide. The non-digestible oligosaccharide may be selected from the group consisting of: fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid oligosaccharides and uronic acid oligosaccharides.

The composition may further include a macronutrient. The macronutrient may be selected from the group consisting of: protein, fat and digestible carbohydrate.

The *Prevotella*-containing composition may comprise dead bacteria, or live bacteria or a mixture of dead and live bacteria. Preferably at least some of the *Prevotella* comprised in the composition are living bacteria. Where provided in the form of a unit dose composition (such as a tablet or capsule) a unit dose may have from about $1 \times 10^6$ to $1 \times 10^{12}$ cfu of *Prevotella*. In other embodiments, a single dosage unit may provide less than $1 \times 10^6$ to $1 \times 10^{12}$ cfu of *Prevotella*, in which case, 2 or more dosage units are required to provide $1 \times 10^6$ to $1 \times 10^{12}$ cfu of *Prevotella*.

In one embodiment there is provided a composition conditioned by a bacteria described above, preferably by *Prevotella copri* bacteria or by a bacteria having a 16S rDNA sequence shown in SEQ ID No:1; or by a bacteria having a 16S rDNA sequence having at least 97% identity, preferably 98% identity, preferably 99% identity with the sequence shown in SEQ ID No:1, or by a bacteria having a 16S rDNA sequence shown in SEQ ID No: 2, or by a bacteria having a 16S rDNA sequence having at least 97% identity, preferably 98% identity, preferably 99% identity with the sequence shown in SEQ ID No:2. The composition may be used in the above described method for minimizing the likelihood of development of allergy in offspring. In one embodiment the composition is acellular. The composition may further comprise a further ingredient that is beneficial for a pregnant or lactating woman selected from the group consisting of a mineral, a vitamin, a long chain polyunsaturated fatty acid, a non-digestible oligosaccharide, or a macronutrient selected from a digestible carbohydrate, a fat or oil and protein.

In the above described embodiments, the composition may be provided in the form of a capsule, tablet, bead or powder or in the form of a food product.

In the above described embodiments where the composition comprises *Prevotella*, especially *Prevotella copri*, the *Prevotella* cells may be dried, may be microencapsulated, may be coated with an enteric coating (as described below), having an enteric coating.

In the above described embodiments where the composition comprises *Prevotella*, especially *Prevotella copri*, may be provided in a form enabling re-hydration before administration.

In one embodiment, the composition may further comprise a desiccant.

In one embodiment, the composition may further comprise an osmoprotectant.

In one embodiment, the composition may further comprise a cryoprotectant.

E. Manufacture

The invention provides a use of *Prevotella* in the manufacture of a composition for administration to a female individual to minimize the likelihood of development of allergy in progeny of the female individual.

*Prevotella copri* may be produced by culture of a strain of bacteria deposited as DSM number 18205 described above.

Alternatively, *Prevotella copri* may be isolated from feces and the isolate used to produce *Prevotella copri* cells in culture. Briefly, 0.5 g of a faecal sample is immediately suspended in dilution buffer and 50 ml $10^8$-diluted faecal sample are plated anaerobically on medium 0.05% glucose, 0.05% cellobiose, 0.05% soluble starch, 3.75% minerals, 0.025% L-cysteine $HCl.H_2O$, 0.0001% resazurin, 0.4% $Na_2CO_3$, 2% trypticase, 0.05%; yeast extract, 0.31% volatile fatty acid, 0.001% hemin, and 2.0% agar. Isolates are subcultured on Eggerth Gagnon (EG) agar supplemented with 5% (v/v) horse blood. Isolates that contain *Prevotella copri* are identified on the basis of containing a 16S nucleotide sequence common to *Prevotella_9* species X as described herein. Preferably the isolate contains OTU000041, more preferably, a nucleic acid having SEQ ID No:1 or SE ID No:2 nucleotide sequence. In this embodiment, it is preferred that the *Prevotella copri* is isolated from the feces or stool of a mother who contains *Prevotella copri* nucleic acid in her stool and who does not have offspring who have allergic disease. Such an individual may be identified by the methods of the invention described above.

*Prevotella copri* strain, whether isolated from faeces, or otherwise may be cultured in 100% $CO_2$ at 37° C. in EG media supplemented with horse blood. Alternatively, cells may be cultured in Columbia blood medium supplemented with 5% defibrinated sheep blood, or PYG medium (modified). The cells may be cultured to an optical density consistent with end of a logarithmic growth phase.

*Prevotella* including *Prevotella* derived from a culture method described above may be dried before, during or at completion of formulation. This may improve viability of *Prevotella* by reducing the water activity of the cells as well as improving the viability and stability of formulations that contain the cells. *Prevotella* may be dried so as to decrease the water or moisture content of *Prevotella* cells to about 1 to 10%, preferably from about 2 to 8%, more preferably from about 2 to 5%. Below 1% there may be reduction in cell viability over long term storage. Above 10% the water activity may be too high resulting in reduction in cell viability.

*Prevotella* may be dried by freeze drying (lyophilization), low temperature vacuum drying (LTVD) or spray drying, or combination of these techniques.

Freeze drying may involve freezing the liquid material in the *Prevotella* cells with further decreases of the chamber pressure enabling frozen water to sublimate. The key advantage is that the drying step is less damaging than techniques that use higher drying temperatures.

A cryoprotectant may be used in a drying process described above such as freeze drying where the purpose is to freeze water in the cells. The purpose the cryoprotectant is to maintain the viability of the cells as the temperature approaches 0° C. or below. This is achieved by lowering the freezing point of water and consequently its vapour pressure. Examples of cryoprotectants include those that are food grade and those that may permeate through the cell wall. Poly-alcohols such as glycerin, sorbitol and mannitol are examples of cryoprotectants. Other cryoprotectants include oligosaccharides such as inulin, starches and dextrin. Trehalose may be used with sugar alcohols, glycerol or certain proteins, particularly milk derived proteins as a cryoprotectant.

LTVD is based on the principle of creating a vacuum to decrease the pressure around the *Prevotella* cells below the vapour pressure of water, which decreases the boiling point of water inside the cells. This condition increases the rate of evaporation of water from cells at a temperature that is lower than would otherwise apply if the desired evaporation rate was to be obtained at standard atmospheric condition. One advantage of LVTD is that temperatures at which ice might form in cells are not reached, so this lessens the likelihood of damage to *Prevotella* cells.

Spray drying is an atomization technology whereby a drying chamber receives a liquid spray containing *Prevotella* cells which is rapidly evaporated as soon as it encounters a hot air flow producing finely dried particles. Spray drying may involve the use of a stream which acts as an osmoprotectant to protect the *Prevotella* cells from over drying. These osmoprotectants may include trehalose, non fat milk solids, or adonitol. The osmoprotectants may encapsulate the *Prevotella* cells as described further below.

During or after drying, *Prevotella* cells may be microencapsulated. Microencapsulation of *Prevotella* cells may assist in maintaining the viability of cells during or after drying. Further, microencapsulation may assist in improving stability during storage of *Prevotella* cells or during passage through the gastro-intestinal tract.

Where microencapsulation occurs during drying, the drying step may serve the dual purposes of reducing water content of cells and forming the structure of the microcapsule.

Microencapsulation may take the form of monocore encapsulation in which each capsule contains a single cell, or polycore encapsulation in which each capsule contains more than one cell. A further form is a matrix encapsulation in which individual cells are entrapped within a polymeric material, examples of which include sugars, polysaccharides, proteins and combinations thereof. Monocore or polycore encapsulated *Prevotella* cells may be entrapped within a polymeric matrix. A microcapsule may have a diameter in the range from 1 micron (monocore encapsulation) through to 1 mm (matrix encapsulation).

Carbohydrate based encapsulates may be used during a freeze drying or spray drying process. Alginate is a common microencapsulation material due to it being nontoxic, relatively cheap and its use in creating matrix microencapsulation in the form of beads. Calcium and sodium alginate are the most widely used forms. Poly-1-lysine alginate composition has also been used for microencapsulation. Alginates are generally used at less than 5% by weight.

Alginate may be combined with cryoprotectants such as glycerol where freeze drying is involved in production, or where *Prevotella* cells are frozen during storage after drying and encapsulation. Other compounds that may be used with alginate to improve survival include antioxidants (such as ascorbic acid) and buffering agents (phosphate containing buffers).

Polysaccharides such as cellulose acetate phthalate, maltodextrin and modified waxy maize starch have been used as microencapsulants, as have low molecular weight sugars (lactose, trehalose, maltose, and sucrose) and poly-alcohols (mannitol and sorbitol).

The carbohydrate used for microencapsulation may be a prebiotic i.e. a compound or composition that provides growth enhancing effects, or is a nutrient for *Prevotella* cells in the gastro-intestinal tract.

Protein based encapsulates may also be used during a preparative process for drying cells. These include skim milk, casein and whey protein or non-milk proteins. Plant based proteins such as soy protein has also been used.

*Prevotella* cells normally inhabit the GI tract in healthy human individuals, including the stomach and duodenal and ileal regions of the small intestine. Endogenous *Prevotella* therefore has an ability to survive in low pH and bile containing environs.

The stability of cells in the gastro-intestinal tract may be enhanced or improved by using a micro-encapsulant that can either minimize exposure to the environment, particularly so as to provide cells with sufficient time to acclimatize to the environment. For example, a microcapsule may gradually expose cells to low pH or bile over a predetermined time period thereby minimizing the likelihood of inducing shock in the cells. For this purpose, cells may be provided in the form of a monocore or polycore microcapsule, or as a matrix microcapsule. Anyone of these forms of microcapsule may be further provided with a coating in the form of a layer located on or about the microcapsule form to assist in maintenance of viability of cells. The coated microcapsule may be provided in the form of a tablet, a capsule or a bead suitable for oral administration.

Enteric coats are often pH selective and allow for protection against gastric pH and that subsequently dissolve in the more alkali intestinal environment. Various forms of hydroxypropyl methylcellulose (HPMC) including HPMC phthalate have been used to protect orally given bacteria. High amylose starch, particularly chemically substituted starch such as carboxymethyl high amylose starch has also been used. The chemical substitution may minimize degradation of starch in the gastric environment, and, being polysaccharide in nature, the starch is quickly dissolved by enzymatic hydrolysis upon reaching the small intestine. Starch has also been combined with chitosan to provide an enteric coating that may substantially resist degradation in the gastric environment and permit release of cells into the intestine or colon.

Compression coatings which erode over time in gastric and intestinal conditions may be utilized. For example a gel layer of alginate may be used alone or combined with other layers of coating formed from chitosan, whey protein, poly-L-Lysine. Alginate may be mixed with glycerol and xanthan gum. Other microencapsulation systems may use milk protein matrices that are induced by rennet, whey proteins, casein and lactoglobulin.

Generally, *Prevotella* cells are stored at room temperature, or 4-7° C., or from 0 to 20° C., depending on prior processing and duration of storage.

Cells are generally dried according to a technique described above before storage. If microencapsulation is implemented, it may be necessary to further dry encapsulated cells so as to remove residual water introduced during encapsulation. Removal of water could be carried out through treatments such as use of a desiccant.

Freeze or spray dried microcapsules having low water activity may be stored for no longer than about 8 to 12 weeks without significant impact on viability. Storage for up to 20 months may be possible at colder temperatures from −20 to 7° C.

The viability of dried and/or encapsulated cells can be determined by counting numbers of colony forming units on media described above. This may involve serial diluting from stock derived from a particular batch of *Prevotella*.

Generally it is preferred that *Prevotella* composition should have sufficient numbers of cells to provide from $10^8$ to $10^9$ cells to the gastro intestinal tract. Therefore where provided in the form of a unit dose composition (such as a tablet or capsule) a unit dose may have from about $1\times10^6$ to $1\times10^{11}$ cfu of *Prevotella*.

The invention will now be described with reference to the following, non-limiting examples.

It will be understood that the invention disclosed and defined in this specification extends to all alternative combinations of two or more individual features mentioned or evident from the text or drawings. All of these different combinations constitute various alternative aspects of the invention.

Example 1

Study Outline

Using an unselected antenatal sampling frame, a birth cohort of 1074 mother-infant pairs in the southeast of Australia was assembled. Infants were excluded if they were born before 32 weeks of gestation, developed a serious illness in the first week of life, or had significant congenital or genetic abnormalities. Women completed a food frequency questionnaire as described previously (McOrist, Abell et al. 2008) and provided a faecal sample at approximately 36 weeks of pregnancy. Flow cytometry was conducted to enumerate immune cells on freshly collected cord blood samples (i.e. at birth). Infants were reviewed in the first days of life and 1, 3, 6, 9 and 12 months after birth. Three case groups (food allergy, atopic eczema and atopic wheeze) were compared with a randomly selected subgroup of 324/894 (36%) infants who completed the 1-year review.

Study Measures: Case Definitions

Food allergy: Skin prick allergy testing (SPT) was performed at 1-year according to standard guidelines (Bernstein and Storms 1995). A positive skin prick test was defined as a wheal diameter at least 2 mm greater than that produced by a negative control solution, measured at 15 minutes. SPT was performed using QUNITIP® devices (skin pricks) to the following allergens: cow's milk, egg, peanut, sesame, cashew, dust mite (*Dermatophagoides pteronyssinus* 1), cat, dog, rye grass and *Alternaria tenius*(Stallergenes®). Infants who exhibited a positive SPT to any of the five foods tested were invited to attend a food allergy clinic for clinical assessment+/−oral food challenge. Infants with a clear history of an immediate-type reaction following exposure to a specific food to which they were skin prick positive were classified as allergic to that food. In the absence of such history, oral food challenges for egg, peanut, sesame and cashew were undertaken regardless of the SPT wheal size (Osborne, Koplin et al. 2010) using standardized food challenge protocols (Koplin, Tang et al. 2011). A positive food challenge was defined according to the protocol established by the HealthNuts study (Osborne, Koplin et al. 2010).

Atopic wheeze: The combination of wheezing illnesses and atopic sensitisation during the first year of postnatal life is associated with a dramatically increased risk of persisting wheeze and asthma in subsequent childhood. Respiratory questionnaires were administered at 1, 3, 6, 9 months and 1 year. At each review parents were provided with a definition of wheeze and then asked whether their child had "wheeze or whistling in the chest since the last review". Atopic wheeze was defined as the presence of parent-reported wheeze during the first year of life plus a positive SPT (2 mm) to any of the food antigens or aeroallergens.

Atopic Eczema. Eczema questionnaires were administered at 1, 3, 6, 9 months and 1 year; and clinical assessments were conducted at 1 month, 6 months and 1 year. Eczema was defined according to the Modified UK working party criteria for infants under 12 months (Williams, Burney et al. 1994, Fleming, Bodner et al. 2001). All infants had to have a history of itchy skin plus at least three of the following: a history of dry skin, a family history of allergy, a history of skin rash affecting the flexures or outer surfaces of the limbs or affecting the head or cheeks, visible dermatitis assessed during a study visit at either 1 month, 6 months or 1 year (Ismail, Oppedisano et al. 2012). Atopic eczema was defined as the presence of eczema plus atopic sensitisation.

Study Measures: Collection and Processing of Maternal Stool Samples

Stool Sample Collection

Stool samples were collected from pregnant women at 36 weeks gestation. Participants were provided with sterile specimen jars and detailed collection instructions. The stool samples were then either: (i) placed into an esky with ice blocks (supplied by BIS team) and brought immediately to the University Hospital, or (ii) stored in the household freezer (approximately −20° C.) until delivery to the University Hospital in an esky with ice blocks. Once samples reached the University Hospital the laboratory staff recorded all the collection details and thawed the samples. They were then aliquoted into 4-6 storage tubes and stored in a−80° C. ultra low temperature freezer until processing.

Protocol for DNA Isolation from Stool Samples

The microbial DNA was extracted using the POWER-SOIL® (DNA Isolation) Kit, Cat #12888-100. The protocol followed the manufacturers instructions and included a minor preparatory pre-lysis step for improved stool disaggregation.

1. Remove an aliquot of stool from the −80° C. freezer and thaw partially.
2. Scrape a small portion (approx. 100-250 mg) of the stool sample and immediately return the remainder of the stool sample to the freezer.
3. Weigh the tube+scrape of stool to determine the sample weight. Record in the table below.
4. Check Solution C1. If Solution C1 is precipitated, heat solution to 60° C. or warm in the 37° C. incubator until dissolved before use.
5. Add 250 ul of MO BIO Lysis Solution C1 and 250 uL of PowerBead solution/buffer from Labelled PowerBead tube. Vortex the tube at maximum speed for 2 minutes to solubilize and pre-lyse the stool sample. Perform a quick spin to remove bubbles.
6. Pipette the total amount of Supernatant (leave the precipitate including fibre) into the labelled MO BIO PowerBead tube that already removed 250 μL of MO BIO solution/buffer. Vortex for 10 seconds.
7. Heat the tubes in a 90C heat block for 5 minutes.
8. Secure the PowerBead tubes horizontally on the MO BIO vortex adapter tube holder and vortex at maximum speed for 10 minutes.
9. Centrifuge tubes at 9,800 g for 1 minute at room temperature (approx. 22C).
10. Transfer 750 ul of the supernatant to a clean labelled 2 ml collection tube (provided in kit).
11. Add 400 ul of Solution C2 (for removal of inhibitors) and vortex well for 10 seconds.
12. Incubate at 4C (in the cool-block kept in the fridge) for 5 minutes.
13. Centrifuge the tubes at room temperature for 2 minute at 14,000 g.
14. Avoiding the pellet, transfer 1000 ul of supernatant to a clean labelled 2 ml collection tube.
15. Add 600 ul of Solution C3 (for further removal of inhibitors) and vortex briefly. Incubate at 4° C. (in the cool-block in the fridge) for 5 minutes.
16. Centrifuge the tubes at room temperature for 2 minute at 14,000 g.
17. Avoiding the pellet, transfer 2×600 ul of supernatant into 2×clean labelled 2 ml collection tube.
18. Shake to mix Solution C4 (DNA binding) before use. Add 1000 ul of Solution C4 to the supernatant in each tube and vortex well for 10 seconds.
19. Load 650 ul (5 separate times) on to a labelled spin filter and centrifuge at 12,200 g for 1 minute at room temperature. Discard the flow through and add the additional volumes and centrifuge again until all the sample has passed through the filter.
20. Add 500 ul of Solution C5 (ethanol wash) directly on to the filter and centrifuge at room temperature for 1 minute at 10,000 g.
21. Discard the flow through.
22. Repeat step 18. Use a new labelled collection tube and centrifuge again at room temperature for 2 minute at 10,000 g (this removes any residual ethanol from the DNA on the filter).
23. Carefully place spin filter in a clean labelled FINAL 2 ml collection tube.
24. Add 60 ul of Solution C6 (elution buffer—this can be warmed in the 37° C. incubator) to the centre of the white filter membrane for elution of the DNA.
25. Cap the tube and allow it to sit at room temperature for 5-10 minutes.
26. Centrifuge at room temperature for 1 minute at 10,000 g.
27. Reload eluted DNA onto filter for higher yield.
28. Re-centrifuge at room temperature for 2 minute at 10,000 g.
29. Discard the spin filter and cap the tube.
30. Measure DNA conc using the Nanodrop and then store tubes of DNA in −80° C. freezer.

DNA samples were diluted to 10 ng/μl and shipped on dry ice to JCVI for 16S sequencing.

Study Measures: Microbiome Composition

Region V4 of the 16S rDNA gene was selected using forward and reverse PCR primers GTGCCAGCMGCCGCGGTAA (SEQ ID NO: 13) and GGACTACHVGGGTWTCTAAT (SEQ ID NO: 14) respectively. Dual index primers were attached to enable multiplex sequencing. The resulting libraries were sequenced on the Illumina MiSeq platform producing paired-end sequences. De-multiplexing and low-quality read filtering were performed in the MiSeq software prior to obtaining FASTQ files describing the reads produced by each sample. Corresponding paired-end reads were merged, filtered (to remove merged reads with mismatches, too many or too few base pairs), clustered into OTUs at 97% identity, OTU representative sequences identified and chimeras removed, all using the Usearch software suite. The mothur software suite was used to assign representative sequences to taxa described in the SILVA v123 Nr99 taxonomic database. The final descriptions of OTUs present in each sample were composed in the Usearch suite.

The above procedure was done with samples of 36 week maternal stool as well as 1, 6 and 12 month infant stools and was done in three separate sequencing runs. This application only relates to maternal samples.

Study Measures: Statistical Analyses

The outcome of microbiome composition analysis is an "OTU table" and a "taxonomy table". The OTU table lists, for each sample, the number of times a DNA sequence corresponding to each OTU has been detected in that sample. The taxonomy table gives a taxonomic assignment for each OTU.

Comparison was made between the distributions of OTUs between stool samples from mothers whose infants went on to be diagnosed as food-allergic, and those whose infants returned negative skin prick tests, at 12 months of age. These comparisons were adjusted for the following process covariates (i) which (of three) batches the sample was sequenced in, (ii) whether the sample had been provided to us fresh or frozen, and (iii) the length of time the sample had been stored at −80C before DNA was extracted.

The statistical software programme R was used for all analyses. The package phyloseq was used to manage the data. The data were further analysed using the packages Voom, edgeR, DESeq2 and metagenomeSeq. Univariate analyses were conducted using all four packages. Voom and DESeq2 for were used in the adjusted analyses.

Results: Maternal 16s rDNA Data

We obtained a median 4025 OTUs from 434 samples of maternal origin. Based on an inspection of the data we excluded samples with fewer than 650 OTUs. We also excluded samples which were technical replicates. With reference to the food allergy analyses, we excluded samples from participants who did not have a definitive determination of food allergy status, or had been included for sequencing other than on the basis of subcohort membership or challenge-proven food allergy.

Figure 4:
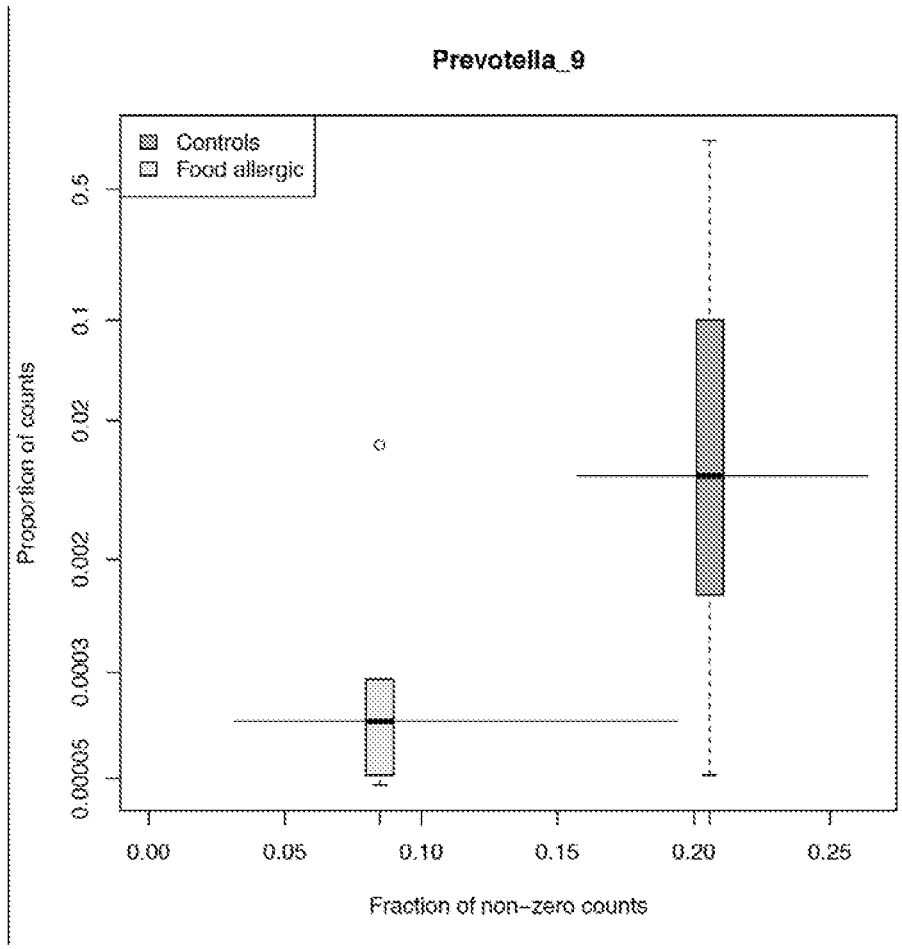
FIG. 4 shows the distribution of the relative abundance of OTUs corresponding the taxa *Prevotella_9* (OTU000041 and OTU000697) in stool samples collected during pregnancy from mothers of infants with subsequent food allergy versus mothers of infants without food allergy.

Using Voom to identify the OTUs most different between the challenge-proven food allergic and not allergic groups identified OTUs 41 and 697 as having the best support (p-values adjusted for multiple testing 0.003 (FIG. 4) and 0.009 respectively; next lowest p-value 0.19). Both these OTUs were classified as *Prevotella_9*, a subgroup of *Prevotella* containing two described species, *Prevotella copri* and *P. paludivivens*. Combining OTUs at the genus level, the *Prevotella_9* subgroup is different between phenotype groups (p=0.005)(FIG. 3). In summary, 48 out of 232 controls, versus 5 of 59 food allergies, had *Prevotella_9* DNA detected, with a total of 33000 detections in the controls versus 44 in the food allergies. Combining subgrouped genera (e.g. all *Prevotella* subgroups into one, and similarly for other genus level taxa with such subgroups) weakens the evidence (p=0.4) (FIG. 4).

An adjusted analysis to consider the effects of duration of storage, whether the sample had been provided to us fresh or frozen, and batch effects showed there was still evidence that *Prevotella_9* was different between the allergy groups (p=0.003) and a similar magnitude of effect.

Figure 5:
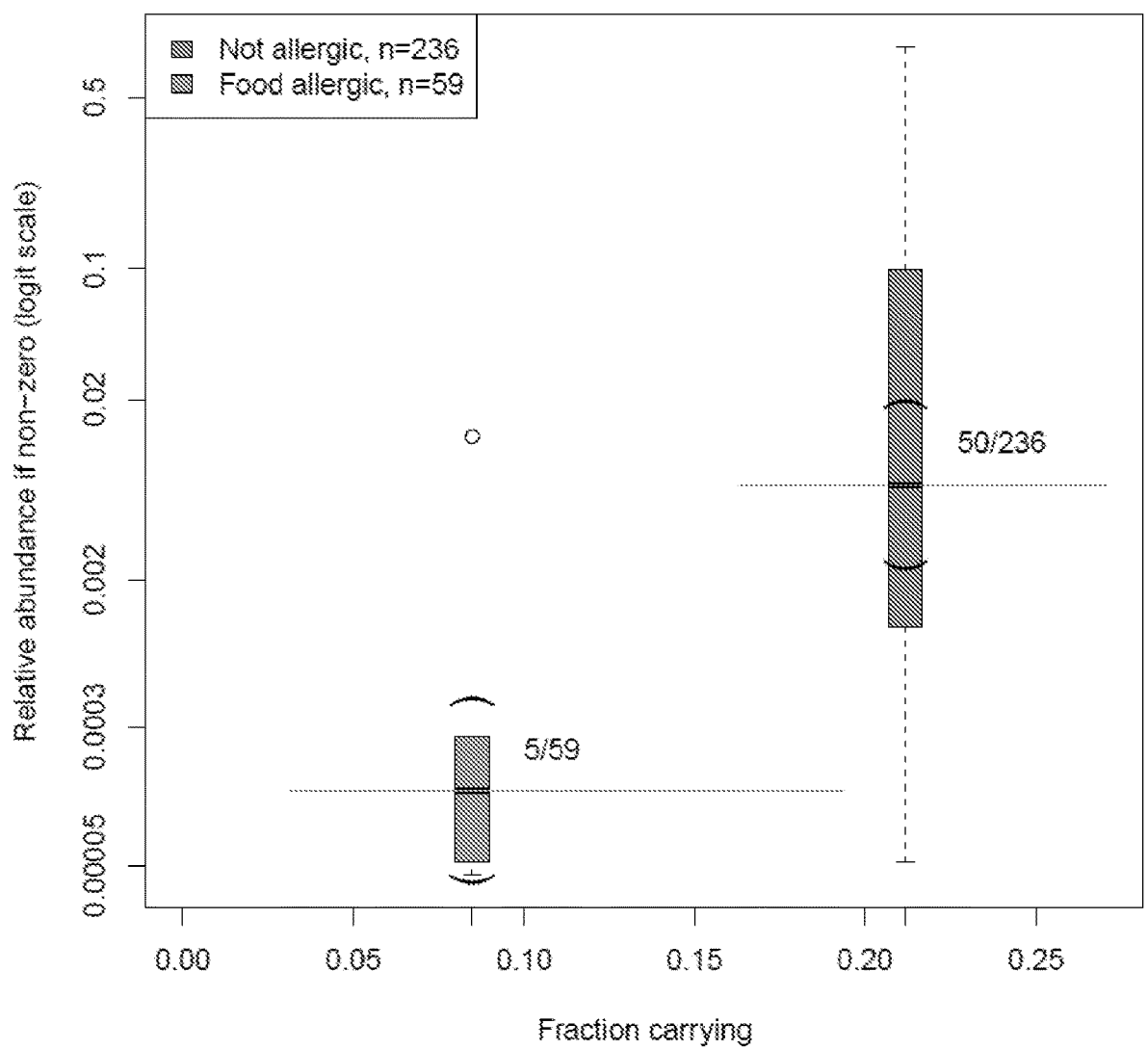
FIG. 5 shows the distribution of the relative abundance of OTU000041 (corresponding to the species *Prevotella copri*) in stool samples collected in pregnancy among mothers of infants with subsequent food allergy versus mothers of infants without food allergy.

We also examined the evidence for OTUs different between the atopic wheeze group and others. For this analysis we included only our random sub cohort. Here again the *Prevotella_9* subgroup had good evidence of a difference between allergic and control groups (p=0.003): it is present in 59 of 262 control samples with 40000 total occurrences, while there is a single occurrence in one member of the atopic wheeze group (14 samples) (FIG. 5).

Figure 6:
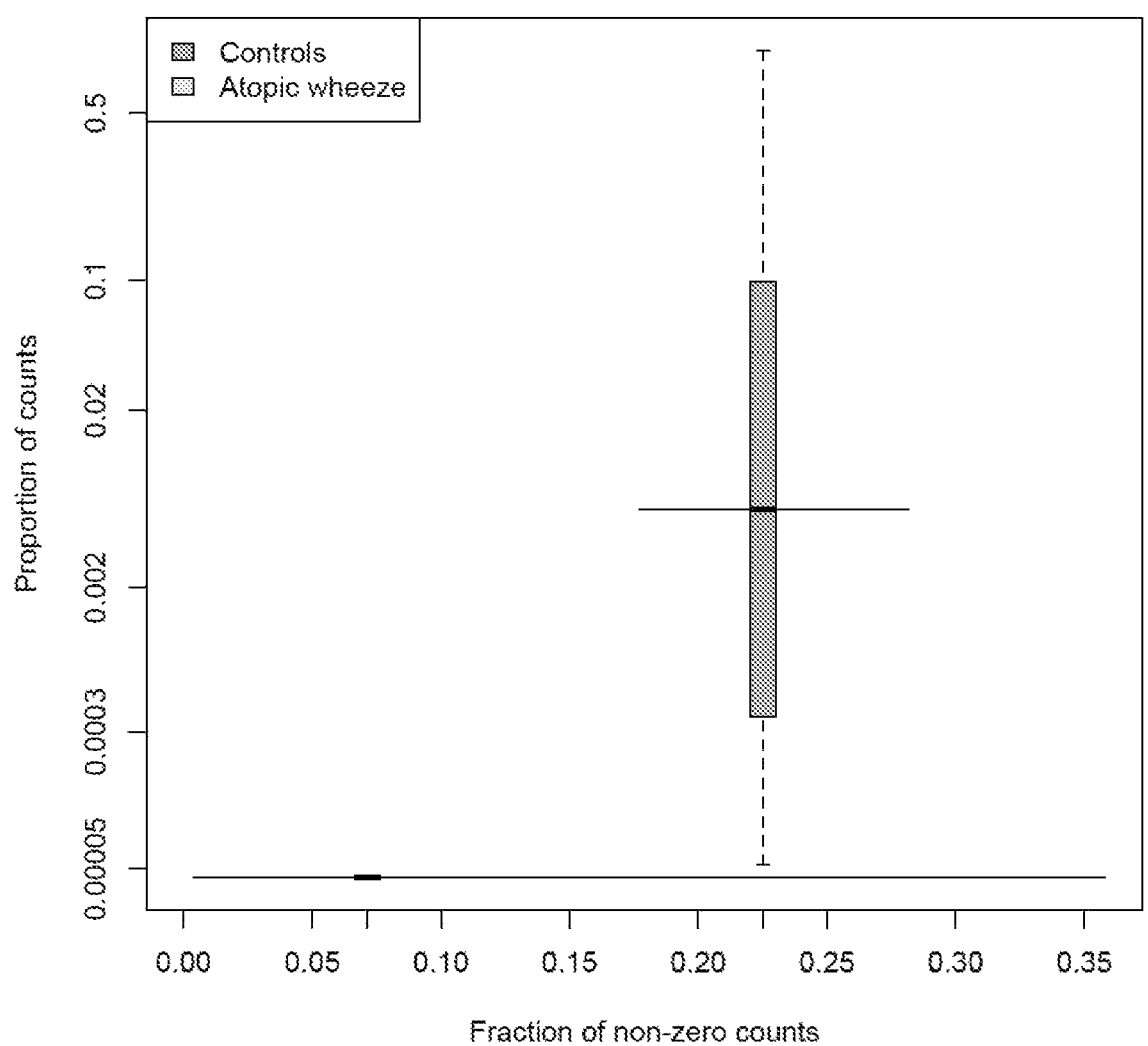
FIG. 6 shows the distribution of the relative abundance of OTUs corresponding the taxa *Prevotella_9* (OTU000041 and OTU000697) in stool samples collected during pregnancy from mothers of infants with atopic wheeze versus mothers of infants without atopic wheeze (controls).
Figure 7:
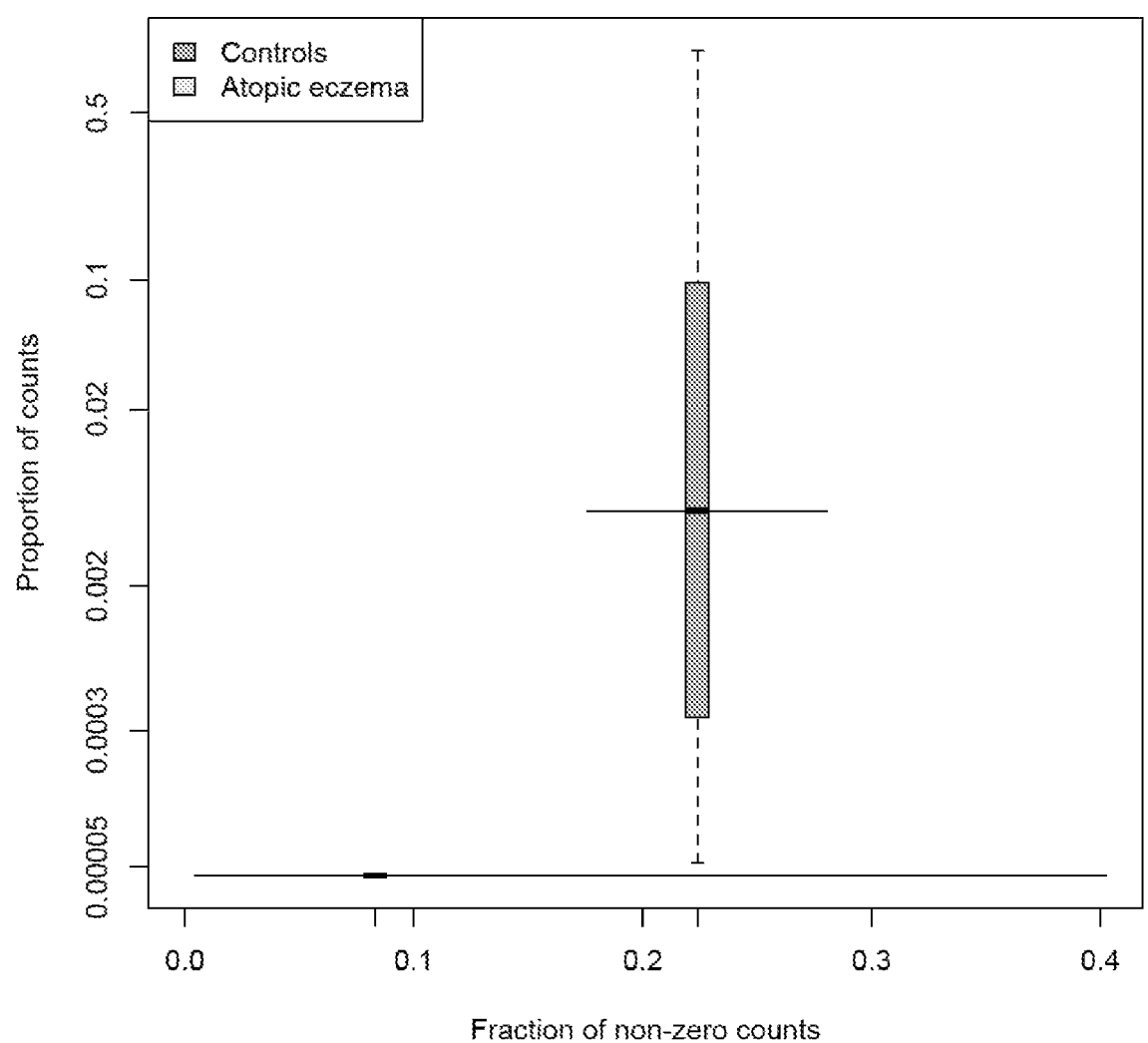
FIG. 7 shows the distribution of the relative abundance of OTUs corresponding the taxa *Prevotella_9* (OTU000041 and OTU000697) in stool samples collected during pregnancy from mothers of infants with atopic eczema versus mothers of infants without atopic eczema (controls).
Figure 8:
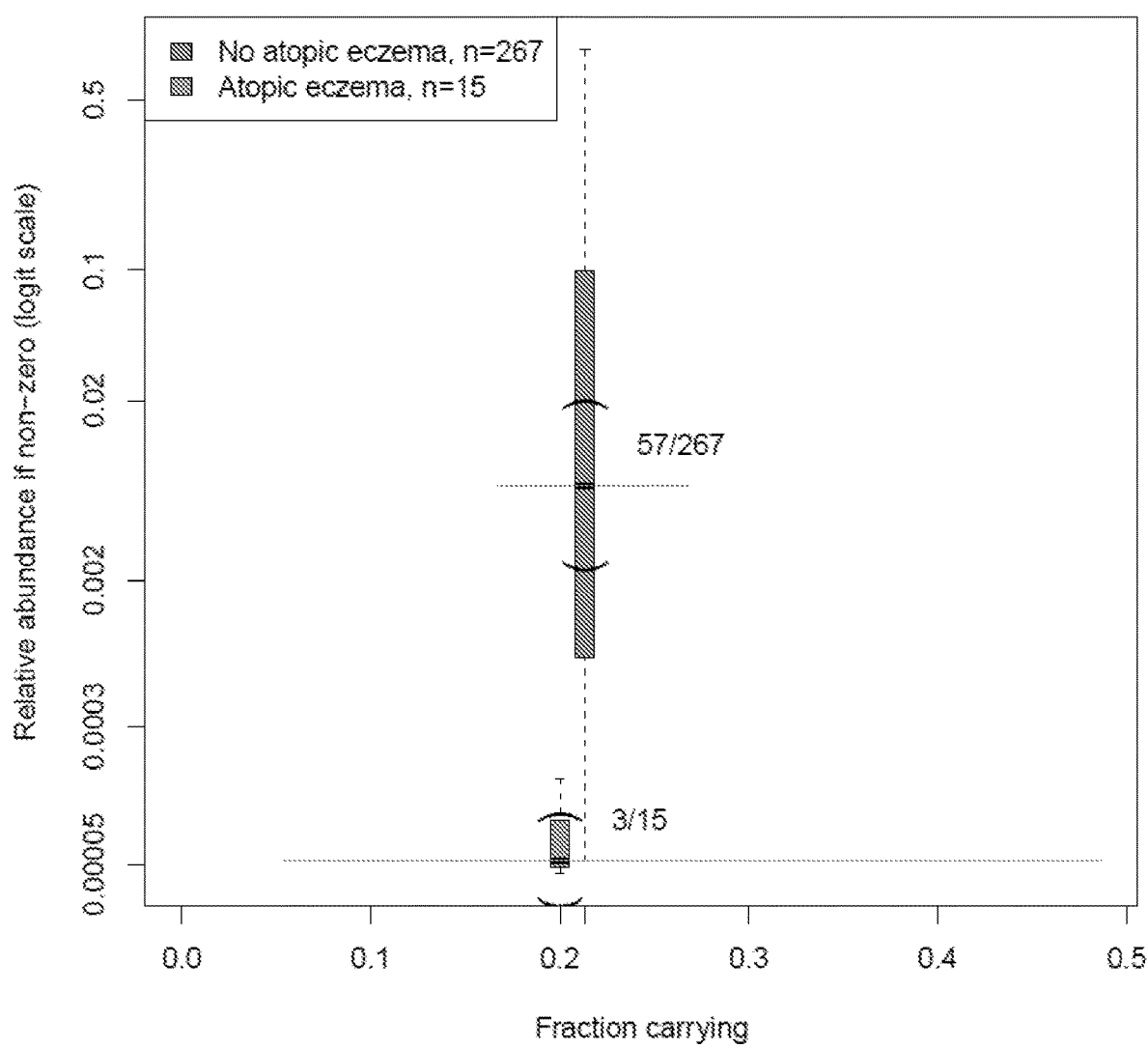
FIG. 8 shows the distribution of the relative abundance of OTU000041 (corresponding to the species *Prevotella copri*) in stool samples collected in pregnancy among mothers of infants with subsequent atopic eczema versus mothers of infants without atopic eczema.
Figure 9:
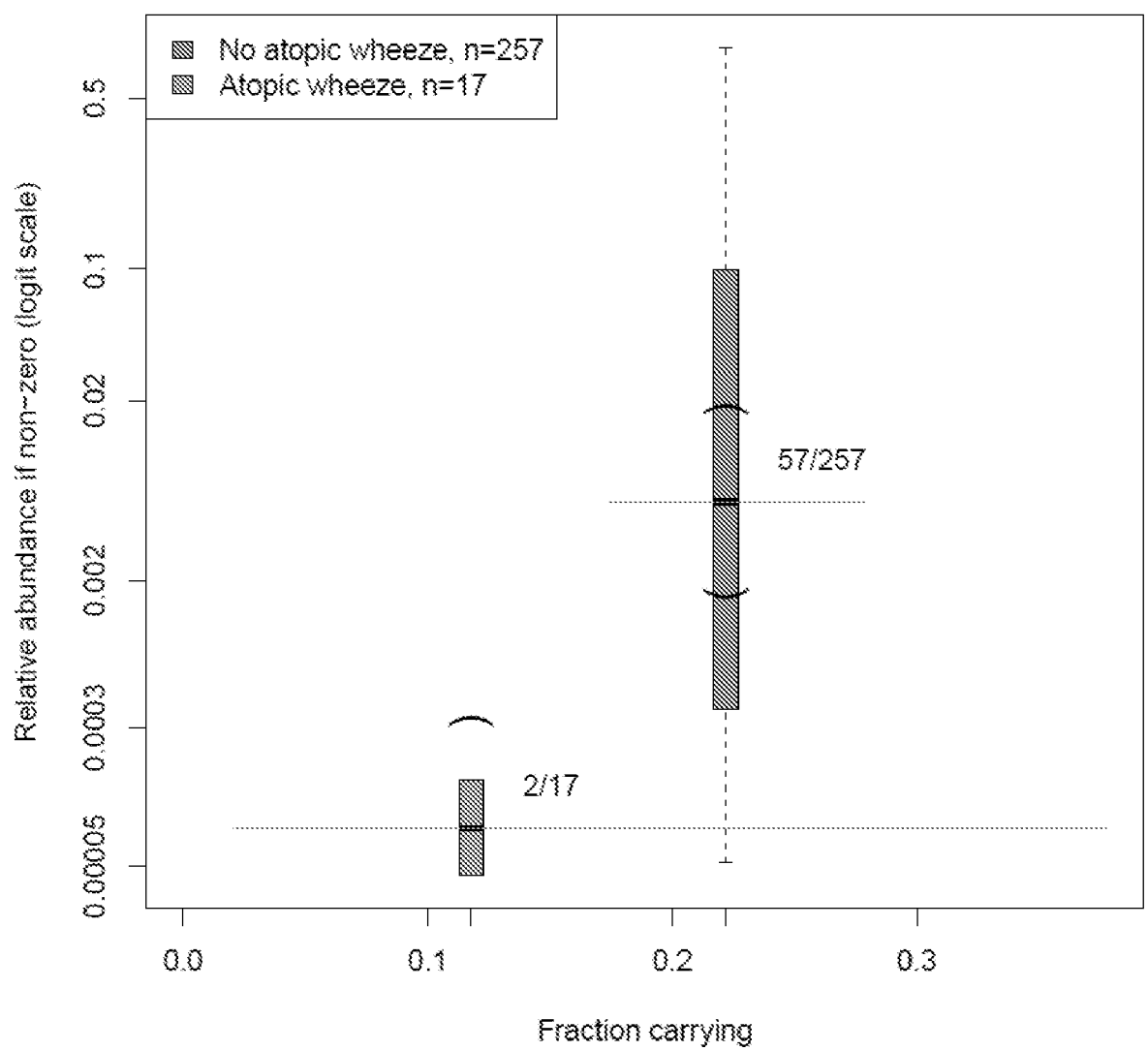
FIG. 9 shows the distribution of the relative abundance of OTU000041 (corresponding to the species *Prevotella copri*) in stool samples collected in pregnancy among mothers of infants with subsequent atopic wheeze versus mothers of infants without atopic wheeze.
Figure 10:
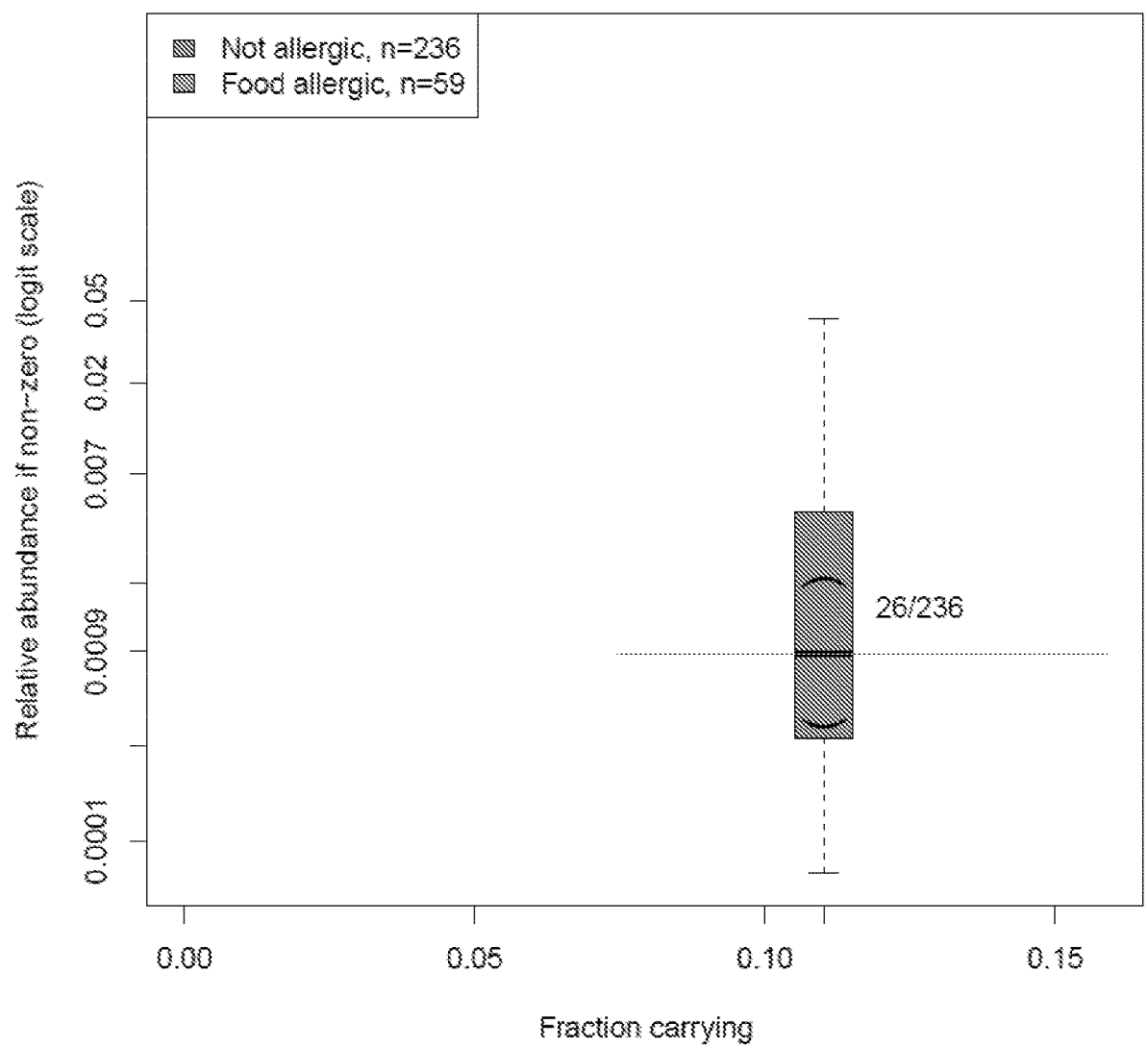
FIG. 10 shows the distribution of the relative abundance of OTU000697 in stool samples collected in pregnancy among mothers of infants with subsequent food allergy versus mothers of infants without food allergy.
Figure 11:
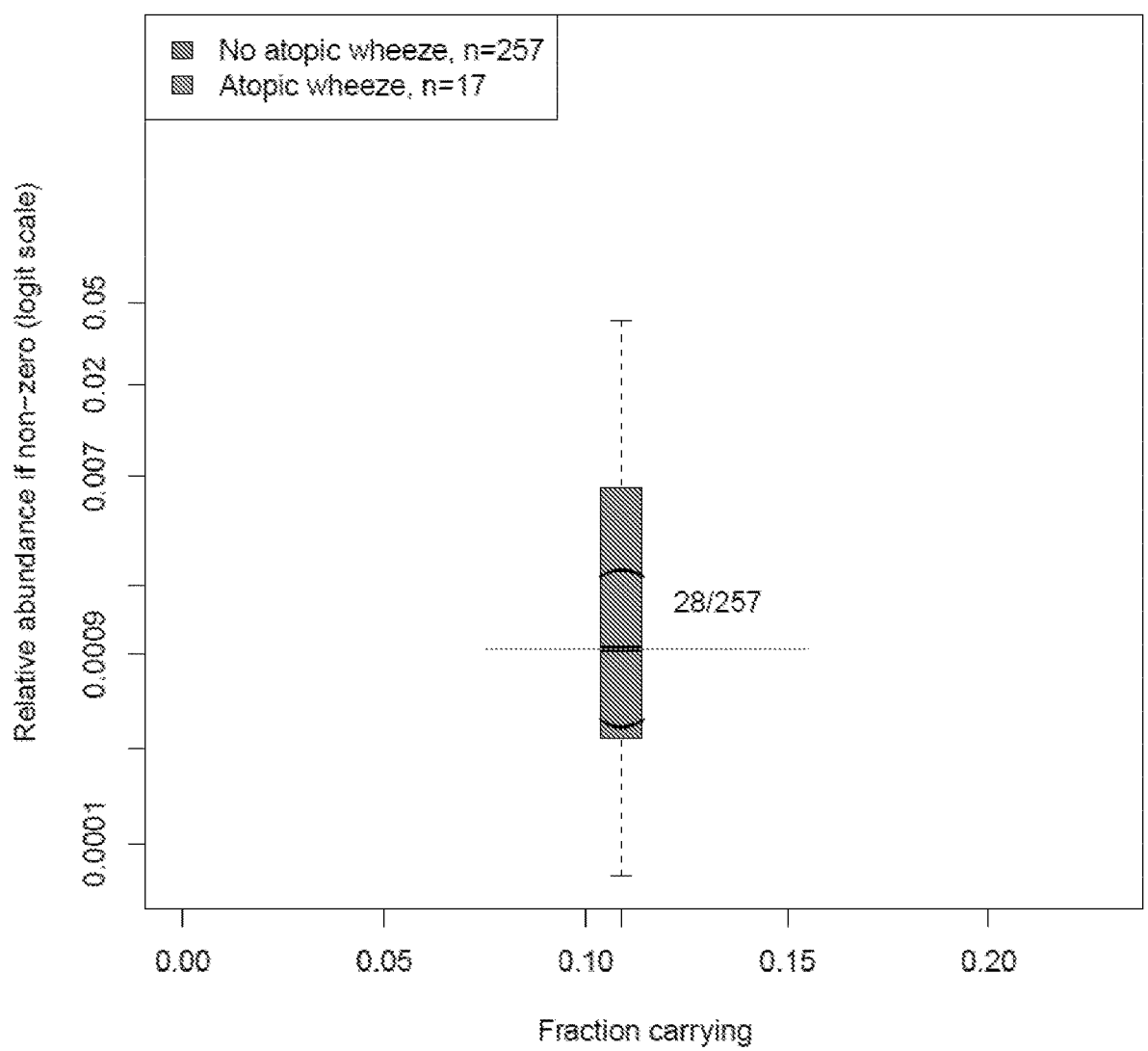
FIG. 11 shows the distribution of the relative abundance of OTU000697 in stool samples collected in pregnancy among mothers of infants with subsequent atopic wheeze versus mothers of infants without atopic wheeze.
Figure 12:
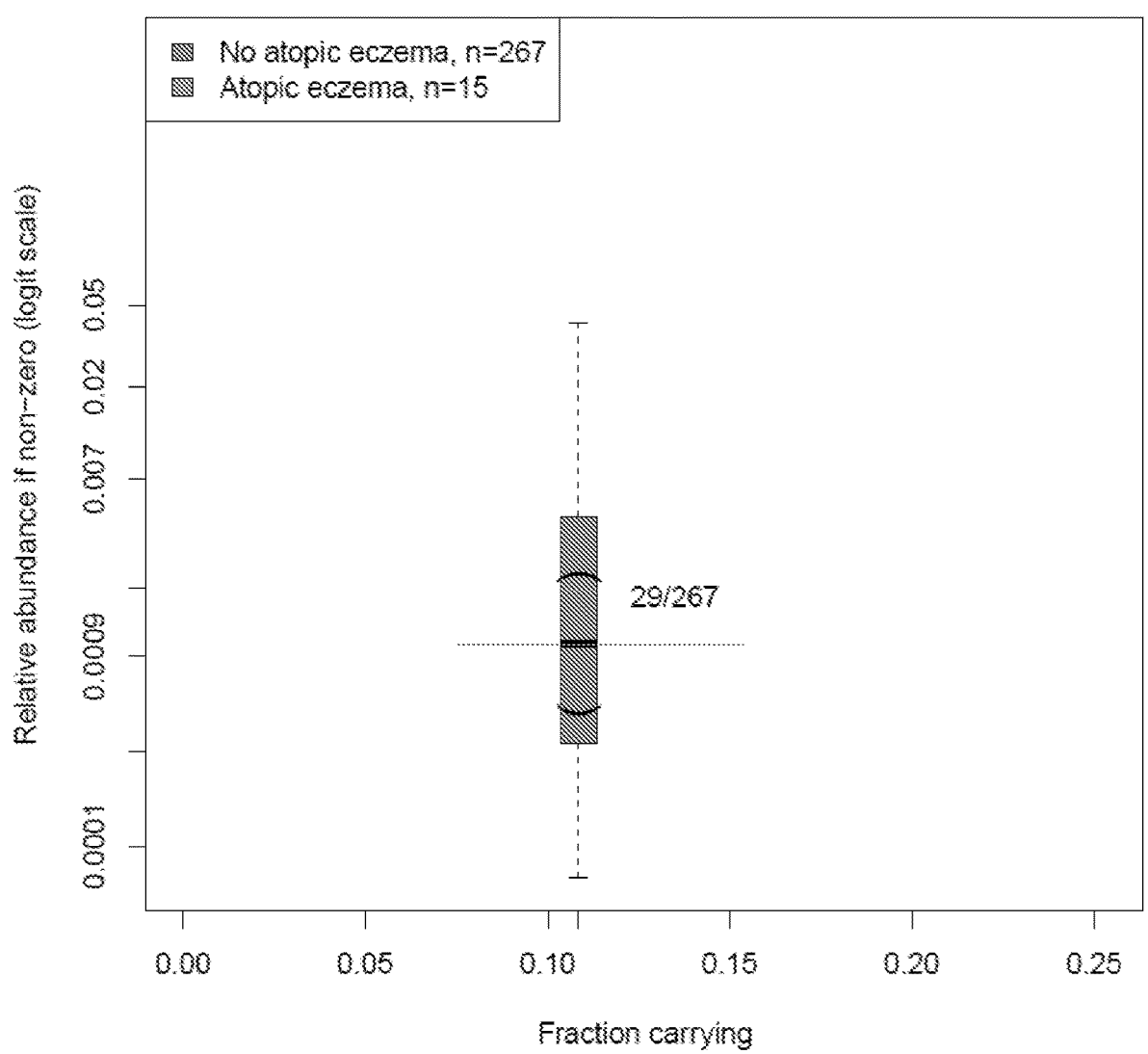
FIG. 12 shows the distribution of the relative abundance of OTU000697 in stool samples collected in pregnancy among mothers of infants with subsequent atopic eczema versus mothers of infants without atopic eczema.

Similarly we looked for differences between the atopic eczema group and others. Here again the *Prevotella_9* subgroup had some evidence of a difference between allergic and control groups (p=0.07); present in 57 of 264 control samples with 39000 occurrences, and a single occurrence in each of two members of the atopic eczema group (FIG. 6).

Results: Confirmation of the Identity of OTU000041

The DNA sequence code of OTU000041 was:

```
                                          (SEQ ID NO: 1)
TACGGAAGGTCCGGGCGTTATCCGGATTTATTGGGTTTAAAGGGAGCGTA

GGCCGGAGATTAAGCGTGTTGTGAAATGTAGACGCTCAACGTCTGCACTG

CAGCGCGAACTGGTTTCCTTGAGTACGCACAAAGTGGGCGGAATTCGTGG

TGTAGCGGTGAAATGCTTAGATATCACGAAGAACTCCGATTGCGAAGGCA

GCTCACTGGAGCGCAACTGACGCTGAAGCTCGAAAGTGCGGGTATCGAAC

AGG
```

Figure 2:
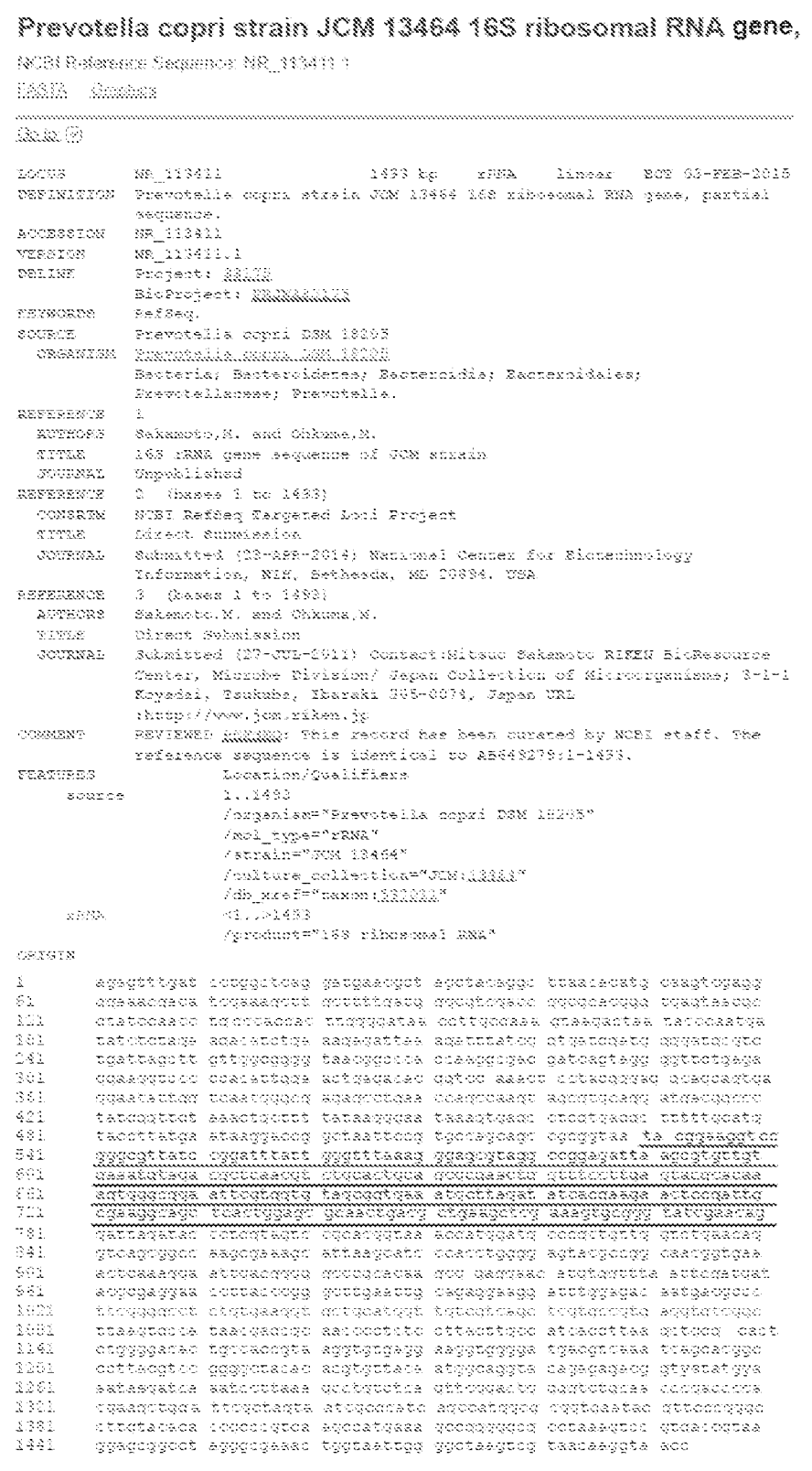

The National Centre for Biotechnology Information BLAST similarity search for OTU000041 in the 16S ribosomal RNA sequences (Bacteria and Archaea) indicates 100% homology with the species *Prevotella copri* strain JCM 13464, the sequence alignment being shown in FIG. 1. The region of homology is in the V4 section of the gene as shown in FIG. 2.

Results: Confirmation of the Identity of OTU000697

The DNA sequence code of OTU000697 was:

```
                                          (SEQ ID NO: 2)
TACGTATGGTGCAAGCGTTATCCGGATTTATTGGGTTTAAAGGGAGCGTA

GGCCGGAGATTAAGCGTGTTGTGAAATGTAGATGCTCAACATCTGAACTG

CAGCGCGAACTGGTTTCCTTGAGTACGCACAAAGTGGGCGGAATTCGTGG
```

-continued
```
TGTAGCGGTGAAATGCTTAGATATCACGAAGAACTCCGATTGCGAAGGCA

GCTCACTGGAGCGCAACTGACGCTGAAGCTCGAAAGTGCGGGTATCGAAC

AGG
```

The sequence is 98% similar to the NR 113411.1 sequence shown in FIG. 1 and to SEQ ID NO: 1).

Example 2

Study Outline: Validation of PCR Assays for the Identification of *Prevotella* 9 Species from Faecal Samples Based on the 16s DNA sequencing data presented above, we have designed PCR assays for the identification of the relevant *Prevotella* 9 species from faecal samples. Primers were designed to amplify DNA regions that match and discriminate OTU000041 and OTU000697. The base pair sequences for the PCR primers are as follows:

```
OTU_41 For
TACGGAAGGTCCGGGCGTTAT

OTU_41 Rev
AGTGCAGACGTTGAGCGTCTA

OTU_697 For
TACGTATGGTGCAAGCGTT

OTU_697 Rev
GCAGTTCAGATGTTGAGCATC
```

Without Limitation the Invention May be Summarised by the Following Items

1. A composition formulated for human consumption (as defined herein) comprising, or consisting of bacteria that is *Prevotella* 9 (as described herein).
2. A composition formulated for human consumption (as defined herein) comprising, or consisting of bacteria comprising:
   a 16S rDNA sequence shown in SEQ ID No:1; or
   a 16S rDNA sequence having at least 97% identity, preferably 98% identity, preferably 99% identity with the sequence shown in SEQ ID No:1; or
   a 16S rDNA sequence shown in SEQ ID No: 2; or
   a 16S rDNA sequence having at least 97% identity, preferably 98% identity, preferably 99% identity with the sequence shown in SEQ ID No:2.
3. A composition according to item 1 or item 2 wherein the bacteria is *Prevotella copri*.
4. A composition according to any one of items 1 to 3 wherein the composition further comprises a further ingredient that is beneficial for a pregnant or lactating woman.
5. A composition according to item 4 wherein the further ingredient is a vitamin selected from the group consisting of: vitamin B1 (thiamine), vitamin B2 (riboflavin), vitamin B3 (niacin), vitamin B5 (pantothenic acid), vitamin B6 (pyridoxine), folic acid, vitamin B12 (cyanocobalamine), biotin, choline, and vitamin C, vitamin D3, vitamin E and vitamin K.
6. A composition according to item 4 or item 5 wherein the further ingredient is a mineral selected from the group consisting of calcium, phosphorus, zinc, iodine, iron, manganese, selenium, copper, and magnesium.
7. A composition according to item 4 or item 5 or item 6 wherein the further ingredient is a long chain polyunsaturated fatty acid (LC-PUFA), preferably eicosapentaenoic acids and/or acyl chain (EPA), docosahexaenoic acid and/or acyl chain (DHA) and arachidonic acid and/or acyl chain (AA).
8. A composition according to item 4 or item 5 or item 6 or item 7 wherein the composition further comprises a further bacteria species, preferably *Lactobacillus accidophilus* group, *L. rhamnosus, L. casei, L. paracasei, L. plantarum, L. reuteri, L. fermentum, Bifidobacterium infantis, B. animalis* subsp. *lactis, B. breve, B. longum* and *B. bifidum*.
9. A composition according to item 4 or item 5 or item 6 or item 7 or item 8 wherein the composition further comprises a non-digestible oligosaccharide, preferably selected from the group consisting of: fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid oligosaccharides and uronic acid oligosaccharides.
10. A composition according to item 4 or item 5 or item 6 or item 7 or item 8 or item 9 wherein the composition further comprises a macronutrient selected from the group consisting of: protein, fat and digestible carbohydrate.
11. A composition according to any one of items 1 to 10 provided in the form of a unit dose composition, preferably as a tablet, or capsule, caplet, bead or powder.
12. A composition according to item 11 wherein the unit dose may have from about $1 \times 10^6$ to $1 \times 10^{11}$ cfu of *Prevotella*
13. A composition conditioned by a bacteria of a composition described above, preferably by *Prevotella copri*.
14. A composition according to item 13 further comprising a further ingredient that is beneficial for a pregnant or lactating woman selected from the group consisting of a mineral, a vitamin, a long chain polyunsaturated fatty acid, a non-digestible oligosaccharide, or a macronutrient selected from a digestible carbohydrate, a fat or oil and protein.
15. A composition according to any one of the preceding items wherein the composition comprises dried bacteria.
16. A composition according to any one the preceding items wherein the bacteria are microencapsulated and/or coated with an enteric coating.
17. A composition according to any one of the preceding items wherein the bacteria may be provided in a form enabling re-hydration before administration.
18. A composition according to any one of the preceding items wherein the composition may further comprise a desiccant, an osmoprotectant or a cryoprotectant.
19. A method for conditioning a female individual (as defined herein) to minimize the likelihood of development of allergy in offspring or progeny of the female individual comprising the step of administering a composition according to any one of the preceding items to the female individual thereby minimizing the likelihood of development of allergy in progeny of the female.
20. A composition according to any one of the preceding items for use by administration to a female individual in minimizing the likelihood of development of allergy in progeny of the female individual.
21. A use of a composition according to any one of the preceding items in a female individual to minimize the likelihood of development of allergy in progeny of the female individual.
22. A method for determining the likelihood of a female individual forming offspring having allergic disease comprising the following steps:
providing a control describing the relative abundance of *Prevotella* 16S rDNA in the stool of a mother who has offspring who do not have allergic disease;
obtaining a sample from the female individual for whom the likelihood of forming offspring having allergic disease is to be determined, thereby forming a test sample;
comparing the test sample with the control to assess whether the test sample has a relative abundance of *Prevotella* 16S rDNA as described in the control;
determining that the female individual has a low likelihood of forming offspring having allergic disease where the test sample has a relative abundance of *Prevotella* 16S rDNA as described in the control
determining that the female individual has a high likelihood of forming offspring having allergic disease where the test sample has a relative abundance of *Prevotella* 16S DNA that is not described in the control.

```
NUCLEOTIDE SEQUENCES:

TACGGAAGGTCCGGGCGTTATCCGGATTTATTGGGTTTAAAGGGAGCGTAGGCCGGAGATTA
AGCGTGTTGTGAAATGTAGACGCTCAACGTCTGCACTGCAGCGCGAACTGGTTTCCTTGAGT
ACGCACAAAGTGGGCGGAATTCGTGGTGTAGCGGTGAAATGCTTAGATATCACGAAGAACTC
CGATTGCGAAGGCAGCTCACTGGAGCGCAACTGACGCTGAAGCTCGAAAGTGCGGGTATCGA
ACAGG (SEQ ID NO: 1)

TACGTATGGTGCAAGCGTTATCCGGATTTATTGGGTTTAAAGGGAGCGTAGGCCGGAGATTA
AGCGTGTTGTGAAATGTAGATGCTCAACATCTGAACTGCAGCGCGAACTGGTTTCCTTGAGT
ACGCACAAAGTGGGCGGAATTCGTGGTGTAGCGGTGAAATGCTTAGATATCACGAAGAACTC
CGATTGCGAAGGCAGCTCACTGGAGCGCAACTGACGCTGAAGCTCGAAAGTGCGGGTATCGA
ACAGG (SEQ ID NO: 2)

TACGGAAGGTCCGGGCGTTAT (SEQ ID NO: 3)

AGTGCAGACGTTGAGCGTCTA (SEQ ID NO: 4)

TACGTATGGTGCAAGCGTT (SEQ ID NO: 5)

GCAGTTCAGATGTTGAGCATC (SEQ ID NO: 6)
```

-continued

NUCLEOTIDE SEQUENCES:

TACGGAAGGTCCGGGCGTTATCCGGATTTATTGGGTTTAAAGGGAGCGTAGGCCGGAGATTA
AGCGTGTTGTGAAATGTAGACGCTCAACGTCTGCACTGCAGCGCGAACTGGTTTCCTTGAGT
ACGCACAAAGTGGGCGGAATTCGTGGTGTAGCGGTGAAATGCTTAGATATCACGAAGAACTC
CGATTGCGAAGGCAGCTCACTGGAGCGCAACTGACGCTGAAGCTCGAAAGTGCGGGTATCGA
ACAG (SEQ ID No: 7)

AGAGTTTGATCCTGGCTCAGGATGAACGCTAGCTACAGGCTTAACACATGCAAGTCGAGG
GGAAACGACATCGAAAGCTTGCTTTTGATGGGCGTCGACCGGCGCACGGGTGAGTAACGC
GTATCCAACCTGCCCAYCACTTGGGGATAACCTTGCGAAAGTAAGACTAATACCCAATGA
TATCTCTAGAAGACATCTGAAAGAGATTAAAGATTTATCGGTGATGGATGGGGATGCGTC
TGATTAGCTTGTTGGCGGGGTAACGGCCCACCAAGGCGACGATCAGTAGGGGTTCTGAGA
GGAAGGTCCCCCACATTGGAACTGAGACACGGTCCAAACTCCTACGGGAGGCAGCAGTGA
GGAATATTGGTCAATGGRCGAGAGCCTGAACCAGCCAAGTAGCGTGCAGGATGACGGCCC
TATGGGTTGTAAACTGCTTTTATAAGGGAATAAAGTGAGCCTCGTGAGGCTTTTTGCATG
TACCTTATGAATAAGGACCGGCTAATTCCGTGCCAGCAGCCGCGGTAATACGGAAGGTCC
GGGCGTTATCCGGATTTATTGGGTTTAAAGGGAGCGTAGGCCGGAGATTAAGCGTGTTGT
GAAATGTAGACGCTCAACGTCTGCACTGCAGCGCGAACTGGTTTCCTTGAGTACGCACAA
AGTGGGCGGAATTCGTGGTGTAGCGGTGAAATGCTTAGATATCACGAAGAACTCCGATTG
CGAAGGCAGCTCACTGGAGCGCAACTGACGCTGAAGCTCGAAAGTGCGGGTATCGAACAG
GATTAGATACCCTGGTAGTCCGCACGGTAAACGATGGATGCCCGCTGTTGGTCTGAACAG
GTCAGCGGCCAAGCGAAAGCATTAAGCATCCCACCTGGGGAGTACGCCGGCAACGGTGAA
ACTCAAAGGAATTGACGGGGGCCCGCACAAGCGGAGGAACATGTGGTTTAATTCGATGAT
ACGCGAGGAAACCTTACCCGGGCTTGAATTGCAGAGGAAGGATTTGGAGACAATGACGCC
CTTCGGGGYCTCTGTGAAGGTGCTGCATGGTTGTCGTCAGCTCGTGCCGTGAGGTGTCGG
CTTAAGTGCCATAACGAGCGCAACCCCTCTCCTTAGTTGCCATCAGGTYAAGCTGGGCAC
TCTGGGGACACTGCCACCGTAAGGTGTGAGGAAGGTGGGGATGACGTCAAATCAGCACGG
CCCTTACGTCCGGGGCTACACACGTGTTACAATGGCAGGTACAGAGAGACGGTYSCYYGY
AAAGTSGATCAAATCCTTAAAGCCTGTCTCAGTTCGGACTGGGGTCTGCAACCCGACCCC
ACGAAGCTGGATTCGCTAGTAATCGCGCATCAGCCATGGCGCGGTGAATACGTTCCCGGG
CCTTGTACACACCGCCCGTCAAGCCATGAAAGCCGGGGCGCCTAAAGTCCGTGACCGTA
AGGAGCGGCCTAGGGCGAAACTGGTAATTGGGCTAAGTCGTAACAAGGTAACC
(SEQ ID No: 8)

AGAGTTTGATCCTGGCTCAGGATGAACGCTAGCTACAGGCTTAACACATGCAAGTCGAGG
GGAAACGACATCGAAAGCTTGCTTTTGATGGGCGTCGACCGGCGCACGGGTGAGTAACGC
GTATCCAACCTGCCCAYCACTTGGGGATAACCTTGCGAAAGTAAGACTAATACCCAATGA
TATCTCTAGAAGACATCTGAAAGAGATTAAAGATTTATCGGTGATGGATGGGGATGCGTC
TGATTAGCTTGTTGGCGGGGTAACGGCCCACCAAGGCGACGATCAGTAGGGGTTCTGAGA
GGAAGGTCCCCCACATTGGAACTGAGACACGGTCCAAACTCCTACGGGAGGCAGCAGTGA
GGAATATTGGTCAATGGRCGAGAGYCTGAACCAGCCAAGTAGCGTGCAGGAWGACGGCCC
TATGGGTTGTAAACTGCTTTTATAAGGGAATAAAGTGAGCCTCGTGAGRCTTTTTGCATG
TACCTTATGAATAAGGACCGGCTAATTCCGTGCCAGCAGCCGCGGTAATACGGAAGGTCC
GGGCGTTATCCGGATTTATTGGGTTTAAAGGGAGCGTAGGCCGGAGATTAAGCGTGTTGT
GAAATGTAGACGCTCAACGTCTGCACTGCAGCGCGAACTGGTTTCCTTGAGTACGCACAA
AGTGGGCGGAATTCGTGGTGTAGCGGTGAAATGCTTAGATATCACGAAGAACTCCGATTG
CGAAGGCAGCTCACTGGAGCGCAACTGACGCTGAAGCTCGAAAGTGCGGGTATCGAACAG
GATTAGATACCCTGGTAGTCCGCACGGTAAACGATGGATGCCCGCTGTTGGTCTGAACAG
GTCAGCGGCCAAGCGAAAGCATTAAGCATCCCACCTGGGGAGTACGCCGGCAACGGTGAA
AACTCAAAGGAATTGACGGGCCCGCACAAGCGGAGGAACATGTGGTTAATTCGATGATA
CGCGAGGAACCTTACCCGGGCTTGAATTGCAGAGGAAGGATTGGAGACAATGACGCCCTT
CGGGGCCTCTGTGAAGGTGCTGCATGGTTGTCGTCAGCTCGTGCCGTGAGGTGTCGGCTT
AAGTGCCATAACGAGCGCAACCCCTCTCCTTAGTTGCCATCAGGTYAWGCTGGGCACTCT
GGGGACACTGCCACCGTAAGGTGTGAGGAAGGTGGGGATGACGTCAAATCAGCAYGGCCC
TTACGTCCGGGGCTACACACGTGTTACAATGGCAGGTACAGAGAGACGGTYSYWYGYAAR
WTSGATCAAATCCTTAAAGCCTGTCTCAGTTCGGACTGGGGTCTGCAACCCGACCCCACG
AAGCTGGATTCGCTAGTAATCGCGCATCAGCCATGGCGCGGTGAATACGTTCCCGGGCCT
TGTACACACCGCCCGTCAAGCCATGAAAGCCGGGGCGCCTAAAGTCCGTGACCGTAAGG
AGCGGCCTAGGGCGAAACTGGTAATTGGGCTAAGTCGTAACAAGGTAACC
(SEQ ID No: 9)

AGAGTTTGATCCTGGCTCAGGATGAACGCTAGCTACAGGCTTAACACATGCAAGTCGAGG
GGAAACGACATCGAAAGCTTGCTTTTGATGGGCGTCGACCGGCGCACGGGTGAGTAACGC
GTATCCAACCTGCCCACCACTTGGGGATAACCTTGCGAAAGTAAGACTAATACCCAATGA
TATCTCTAGAAGACATCTGAAAGAGATTAAAGATTTATCGGTGATGGATGGGGATGCGTC
TGATTAGCTTGTTGGCGGGGTAACGGCCCACCAAGGCGACGATCAGTAGGGGTTCTGAGA
GGAAGGTCCCCCACATTGGAACTGAGACACGGTCCAAACTCCTACGGGAGGCAGCAGTGA
GGAATATTGGTCAATGGRCGAGAGYCTGAACCAGCCAAGTAGCGTGCAGGAWGACGGCCC
TATGGGTTGTAAACTGCTTTTATAAGGGAATAAAGTGAGCCTCGTGAGRCTTTTTGCATG
TACCTTATGAATAAGGACCGGCTAATTCCGTGCCAGCAGCCGCGGTAATACGGAAGGTCC
GGGCGTTATCCGGATTTATTGGGTTTAAAGGGAGCGTAGGCCGGAGATTAAGCGTGTTGT
GAAATGTAGACGCTCAACGTCTGCACTGCAGCGCGAACTGGTTTCCTTGAGTACGCACAA
AGTGGGCGGAATTCGTGGTGTAGCGGTGAAATGCTTAGATATCACGAAGAACTCCGATTG
CGAAGGCAGCTCACTGGAGCGCAACTGACGCTGAAGCTCGAAAGTGCGGGTATCGAACAG
GATTAGATACCCTGGTAGTCCGCACGGTAAACGATGGATGCCCGCTGTTGGTCTGAACAG
GTCAGCGGCCAAGCGAAAGCATTAAGCATCCCACCTGGGGAGTACGCCGGCAACGGTGAA
ACTCAAAGGAATTGACGGGGGCCCGCACAAGCGGAGGAACATGTGGTTTAATTCGATGAT

NUCLEOTIDE SEQUENCES:

```
ACGCGAGGAACCTTACCCGGGCTTGAATTGCAGAGGAAGGATTTGGAGACAATGACGCCC
TTCGGGGYCTCTGTGAANGTGCTGCATGGTTGTCGTCAGCTCGTGCCGTGAGGTGTCGGC
TTAAGTGCCATAACGAGCGCAACCCCTCTCCTTAGTTGCCATCAGGTCAAGCTGGGCACT
CTGGGGACACTGCCACCGTAAGGTGTGAGGAAGGTGGGGATGACGTCAAATCAGCACGGC
CCTTACGTCCGGGGCTACACACGTGTTACAATGGCAGGTACAGAGAGACGGTYSYWTGYA
ARWTSGATCAAATCCTTAAAGCCTGTCTCAGTTCGGACTGGGGTCTGCAACCCGACCCCA
CGAAGCTGGATTCGCTAGTAATCGCGCATCAGCCATGGCGCGGTGAATACGTTCCCGGGC
CTTGTACACACCGCCCGTCAAGCCATGAAAGCCGGGGGCGCCTAAAGTCCGTGACCGTAA
GGAGCGGCCTAGGGCGAAACTGGTAATTGGGGCTAAGTCGTAACAAGGTAACC
(SEQ ID No: 10)

AGAGTTTGATCCTGGCTCAGGATGAACGCTAGCTACAGGCTTAACACATGCAAGTCGAGG
GGAAACGACATCGAAAGCTTGCTTTTGATGGGCGTCGACCGGCGCACGGGTGAGTAACGC
GTATCCAACCTGCCCAYCACTTGGGGATAACCTTGCGAAAGTAAGACTAATACCCAATGA
TATCTCTAGAAGACATCTGAAAGAGATTAAAGATTTATCGGTGATGGATGGGGATGCGTC
TGATTAGCTTGTTGGCGGGGTAACGGCCCACCAAGGCGACGATCAGTAGGGGTTCTGAGA
GGAAGGTCCCCCACATTGGAACTGAGACACGGTCCAAACTCCTACGGGAGGCAGCAGTGA
GGAATATTGGTCAATGGRCGAGAGYCTGAACCAGCCAAGTAGCGTGCAGGATGACGGCCC
TATGGGTTGTAAACTGCTTTTATAAGGGAATAAAGTGAGCCTCGTGAGRCTTTTTGCATG
TACCTTATGAATAAGGACCGGCTAATTCCGTGCCAGCAGCCGCGGTAATACGGAAGGTCC
GGGCGTTATCCGGATTTATTGGGTTTAAAGGGAGCGTAGGCCGGAGATTAAGCGTGTTGT
GAAATGTAGACGCTCAACGTCTGCACTGCAGCGCGAACTGGTTTCCTTGAGTACGCACAA
AGTGGGCGGAATTCGTGGTGTAGCGGTGAAATGCTTAGATATCACGAAGAACTCCGATTG
CGAAGGCAGCTCACTGGAGCGCAACTGACGCTGAAGCTCGAAAGTGCGGGTATCGAACAG
GATTAGATACCCTGGTAGTCCGCACGGTAAACGATGGATGCCCGCTGTTGGTCTGAACAG
GTCAGCGGCCAAGCGAAAGCATTAAGCATCCCACCTGGGGAGTACGCCGGCAACGGTGAA
ACTCAAAGGAATTGACGGGGGCCCGCACAAGCGGAGGAACATGTGGTTTAATTCGATGAT
ACGCGAGGAACCTTACCCGGGCTTGAATTGCAGAGGAAGGATTTGGAGACAATGACGCCC
TTCGGGGYCTCTGTGAAGGTGCTGCATGGTTGTCGTCAGCTCGTGCCGTGAGGTGTCGGC
TTAAGTGCCATAACGAGCGCAACCCCTCTCCTTAGTTGCCATCAGGTYAAGCTGGGCACT
CTGGGGACACTGCCACCGTAAGGTGTGAGGAAGGTGGGGATGACGTCAAATCAGCACGGC
CCTTACGTCCGGGGCTACACACGTGTTACAATGGCAGGTACAGAGAGACGGTYSYWYGYA
ARWTSGATCAAATCCTTAAAGCCTGTCTCAGTTCGGACTGGGGTCTGCAACCCGACCCCA
CGAAGCTGGATTCGCTAGTAATCGCGCATCAGCCATGGCGCGGTGAATACGTTCCCGGGC
CTTGTACACACCGCCCGTCAAGCCATGAAAGCCGGGGGCGCCTAAAGTCCGTGACCGTAA
GGAGCGGCCTAGGGCGAAACTGGTAATTGGGGCTAAGTCGTAACAAGGTAACC
(SEQ ID No: 11)

AGAGTTTGATCCTGGCTCAGGATGAACGCTAGCTACAGGCTTAACACATGCAAGTCGAGG
GGAAACGACATCGAAAGCTTGCTTTTGATGGGCGTCGACCGGCGCACGGGTGAGTAACGC
GTATCCAACCTGCCCACCACTTGGGGATAACCTTGCGAAAGTAAGACTAATACCCAATGA
TATCTCTAGAAGACATCTGAAAGAGATTAAAGATTTATCGGTGATGGATGGGGATGCGTC
TGATTAGCTTGTTGGCGGGGTAACGGCCCACCAAGGCGACGATCAGTAGGGGTTCTGAGA
GGAAGGTCCCCCACATTGGAACTGAGACACGGTCCAAACTCCTACGGGAGGCAGCAGTGA
GGAATATTGGTCAATGGRCGAGAGYCTGAACCAGCCAAGTAGCGTGCAGGAWGACGGCCC
TATGGGTTGTAAACTGCTTTTATAAGGGAATAAAGTGAGYCTCGTGAGRCTTTTTGCATG
TACCTTATGAATAAGGACCGGCTAATTCCGTGCCAGCAGCCGCGGTAATACGGAAGGTCC
GGGCGTTATCCGGATTTATTGGGTTTAAAGGGAGCGTAGGCCGGAGATTAAGCGTGTTGT
GAAATGTAGACGCTCAACGTCTGCACTGCAGCGCGAACTGGTTTCCTTGAGTACGCACAA
AGTGGGCGGAATTCGTGGTGTAGCGGTGAAATGCTTAGATATCACGAAGAACTCCGATTG
CGAAGGCAGCTCACTGGAGCGCAACTGACGCTGAAGCTCGAAAGTGCGGGTATCGAACAG
GATTAGATACCCTGGTAGTCCGCACGGTAAACGATGGATGCCCGCTGTTGGTCTGAACAG
GTCAGCGGCCAAGCGAAAGCATTAAGCATCCCACCTGGGGAGTACGCCGGCAACGGTGAA
ACTCAAAGGAATTGACGGGGGCCCGCACAAGCGGAGGAACATGTGGTTTAATTCGATGAT
ACGCGAGGAACCTTACCCGGGCTTGAATTGCAGAGGAAGGATTTGGAGACAATGACGCCC
TTCGGGGCCTCTGTGAAGGTGCTGCATGGTTGTCGTCAGCTCGTGCCGTGAGGTGTCGGC
TTAAGTGCCATAACGAGCGCAACCCCTCTCCTTAGTTGCCATCAGGTYAAGCTGGGCACT
CTGGGGACACTGCCACCGTAAGGTGTGAGGAAGGTGGGGATGACGTCAAATCAGCACGGC
CCTTACGTCCGGGGCTACACACGTGTTACAATGGCAGGTACAGAGAGACGGTYSYWTGYA
ARWWSGATCAAATCCTTAAAGCCTGTCTCAGTTCGGACTGGGGTCTGCAACCCGACCCCA
CGAAGCTGGATTCGCTAGTAATCGCGCATCAGCCATGGCGCGGTGAATACGTTCCCGGGC
CTTGTACACACCGCCCGTCAAGCCATGAAAGCCGGGGGCGCCTAAAGTCCGTGACCGTAA
GGAGCGGCCTAGGGCGAAACTGGTAATTGGGGCTAAGTCGTAACAAGGTAACC
(SEQ ID No: 12)
```

REFERENCES

Williams, H. C., P. G. Burney, A. C. Pembroke and R. J. Hay (1994). "The U. K. Working Party's Diagnostic Criteria for Atopic Dermatitis. III. Independent hospital validation." Br J Dermatol 131(3): 406-416.

Fleming, S., C. Bodner, G. Devereux, G. Russell, D. Campbell, D. Godden and A. Seaton (2001). "An application of the United Kingdom Working Party diagnostic criteria for atopic dermatitis in Scottish infants." J Invest Dermatol 117(6): 1526-1530.

McOrist, A. L., G. C. Abell, C. Cooke and K. Nyland (2008).

Bernstein, I. L. and W. W. Storms (1995). "Practice parameters for allergy diagnostic testing. Joint Task Force on Practice Parameters for the Diagnosis and Treatment of Asthma. The American Academy of Allergy, Asthma and Immunology and the American College of Allergy, Asthma and Immunology." Ann Allergy Asthma Immunol 75(6 Pt 2): 543-625.

Koplin, J. J., M. L. Tang, P. E. Martin, N. J. Osborne, A. J. Lowe, A. L. Ponsonby, M. N. Robinson, D. Tey, L. Thiele, D. J. Hill, L. C. Gurrin, M. Wake, S. C. Dharmage and K. J. Allen (2011). "Predetermined challenge eligibility and cessation criteria for oral food challenges in the Health-Nuts population-based study of infants." J Allergy Clin Immunol 129(4): 1145-1147.

Osborne, N. J., J. J. Koplin, P. E. Martin, L. C. Gurrin, L. Thiele, M. L. Tang, A. L. Ponsonby, S. C. Dharmage, K. J. Allen and I. HealthNuts Study (2010). "The HealthNuts population-based study of paediatric food allergy: validity, safety and acceptability." Clin Exp Allergy 40(10): 1516-1522. (1993). "Severity scoring of atopic dermatitis: the SCORAD index. Consensus Report of the European Task Force on Atopic Dermatitis." Dermatology 186(1): 23-31.

Ismail, I. H., F. Oppedisano, S. J. Joseph, R. J. Boyle, P. V. Licciardi, R. M. Robins-Browne and M. L. Tang (2012). "Reduced gut microbial diversity in early life is associated with later development of eczema but not atopy in high-risk infants." Pediatr Allergy Immunol 23(7): 674-681.

Rubin, D. B. and R. J. Little (2002). "Statistical analysis with missing data." Hoboken, N.J.: J Wiley & Sons.

Usearch: Edgar, R C (2010) Search and clustering orders of magnitude faster than BLAST, Bioinformatics 26(19), 2460-2461. doi: 10.1093/bioinformatics/btq461

Mothur: Schloss, P. D., et al., Introducing mothur: Open-source, platform-independent, community-supported software for describing and comparing microbial communities. Appl Environ Microbiol, 2009. 75(23):7537-41.

SILVA: Quast C, Pruesse E, Yilmaz P, Gerken J, Schweer T, Yarza P, Peplies J, Glockner F O (2013) The SILVA ribosomal RNA gene database project: improved data processing and web-based tools. Nucl. Acids Res. 41 (Dl): D590-D596.

R: R Core Team (2016). R: A language and environment for statistical computing. R Foundation for Statistical Computing, Vienna, Austria. https://www.R pr jcct. rg/www.R-project.org.

phyloseq: phyloseq: An R package for reproducible interactive analysis and graphics of microbiome census data. Paul J. McMurdie and Susan Holmes (2013) PLoS ONE 8(4):e61217.

voom: Ritchie, M. E., Phipson, B., Wu, D., Hu, Y., Law, C. W., Shi, W., and Smyth, G. K. (2015). limma powers differential expression analyses for RNA-sequencing and microarray studies. Nucleic Acids Research 43(7), e47.

edgeR: Robinson M D, McCarthy D J and Smyth G K (2010). edgeR: a Bioconductor package for differential expression analysis of digital gene expression data. Bioinformatics 26, 139-140

McCarthy D J, Chen Y and Smyth G K (2012). Differential expression analysis of multifactor RNA-Seq experiments with respect to biological variation. Nucleic Acids Research 40, 4288-4297

DESeq2: Michael I Love, Wolfgang Huber and Simon Anders (2014): Moderated estimation of fold change and dispersion for RNA-Seq data with DESeq2. Genome Biology 15, 550 metagenomeSeq: J N Paulson, O C Stine, H C Bravo, M Pop. Differential abundance analysis for microbial marker-gene surveys. Nat Meth Accepted Altschul, S. F., Gish, W., Miller, W., Myers, E. W. & Lipman, D. J. (1990) "Basic local alignment search tool." J. Mol. Biol. 215: 403-410. PubMed Gish, W. & States, D. J. (1993) "Identification of protein coding regions by database similarity search." Nature Genet. 3:266-272. PubMed Madden, T. L., Tatusov, R. L. & Zhang, J. (1.996) "Applications of network BLAST server" Meth. Enzymol. 266: 131-141. PubMed Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402. PubMed Zhang Z., Schwartz S., Wagner L., & Miller W. (2000), "A greedy algorithm for aligning DNA sequences" J Comput Biol 2000; 7(1-2):203-14. PubMed Zhang, 3. & Madden, T. L. (1997) "PowerBLAST: A new network BLAST application for interactive or automated sequence analysis and annotation." Genome Res. 7:649-656. PubMed Morgulis A., Coulouris G., Raytselis Y., Madden T. L., Agarwala R., & Schaffer A. A. (2008) "Database indexing for production MegaBLAST searches." Bioinformatics 15:1757-1764. PubMed Camacho C., Colouris G., Avagyan V., Ma N., Papadopoulos J., Bealer K., & Madden T. L. (2008) "BLAST+: architecture and applications." BMC Bioinformatics 10:421. PubMed Boratyn G M, SchAffer A A, Agarwala R, Altschul S F, Lipman D J, & Madden T. L. (2012) "Domain enhanced lookup time accelerated BLAST." Biol. Direct. 2012 Apr. 17; 7:12. PubMed

The invention claimed is:

1. A method for minimizing the likelihood of development of allergy in offspring of a female individual comprising the step of administering a therapeutically effective amount of *Prevotella* to a female individual to provide from $1 \times 10^6$ to $1 \times 10^{11}$ colony forming units (cfu) per day to the female individual, thereby minimizing the likelihood of development of allergy in an offspring of the female individual, wherein the female individual is administered with *Prevotella* no more than about 6 months prior to her falling pregnant, and wherein the *Prevotella* is *Prevotella_9*, species X or species Y.

2. The method of claim 1, wherein the female individual is administered with *Prevotella_9* 1 to 3 months prior to her falling pregnant.

3. The method of claim 1, wherein the female individual is administered with *Prevotella* 9 in the 1st, 2nd or 3rd trimester, or in all trimesters.

4. The method of claim 3, wherein the *Prevotella_9* is administered for at least 2 months before delivery.

5. The method of claim 1, wherein the *Prevotella_a* is administered once or twice daily or once every 2 or 3 days, or once weekly.

6. The method of claim 1, wherein the *Prevotella_9* is provided orally to the female individual in the form of a capsule, tablet or like formulation adapted for oral administration, or in the form of a food or beverage.

7. The method of claim 1, wherein the *Prevotella_9* species X is OTU000041 or SEQ ID NO: 1.

8. The method of claim 7, wherein the *Prevotella_9* species X is *Prevotella copri*.

9. The method of claim 1, wherein the *Prevotella_9* species Y is OTU000697 or SEQ ID NO: 2.

* * * * *

UNITED STATES PATENT AND TRADEMARK OFFICE
CERTIFICATE OF CORRECTION

PATENT NO. : 11,529,380 B2
APPLICATION NO. : 16/471058
DATED : December 20, 2022
INVENTOR(S) : Peter Vuillermin, Anne-Louise Ponsonby and Mimi Tang It is certified that error appears in the above-identified patent and that said Letters Patent is hereby corrected as shown below:

In the Claims

In Claim 3, Column 49, Line 59, delete "Prevotella 9" and insert -- Prevotella_9 -- therefor.

In Claim 5, Column 50, Line 46, delete "Prevotella_a" and insert -- Prevotella_9 -- therefor.

Signed and Sealed this
Fourteenth Day of March, 2023

*Katherine Kelly Vidal*

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 253
<212> TYPE: DNA
<213> ORGANISM: Prevotella

<400> SEQUENCE: 1

```
tacggaaggt ccgggcgtta tccggattta ttgggtttaa agggagcgta ggccggagat      60
taagcgtgtt gtgaaatgta gacgctcaac gtctgcactg cagcgcgaac tggtttcctt     120
gagtacgcac aaagtgggcg gaattcgtgg tgtagcggtg aaatgcttag atatcacgaa     180
```

```
gaactccgat tgcgaaggca gctcactgga gcgcaactga cgctgaagct cgaaagtgcg    240
ggtatcgaac agg                                                       253

<210> SEQ ID NO 2
<211> LENGTH: 253
<212> TYPE: DNA
<213> ORGANISM: Prevotella

<400> SEQUENCE: 2
tacgtatggt gcaagcgtta tccggattta ttgggtttaa agggagcgta ggccggagat    60
taagcgtgtt gtgaaatgta gatgctcaac atctgaactg cagcgcgaac tggtttcctt    120
gagtacgcac aaagtgggcg gaattcgtgg tgtagcggtg aaatgcttag atatcacgaa    180
gaactccgat tgcgaaggca gctcactgga gcgcaactga cgctgaagct cgaaagtgcg    240
ggtatcgaac agg                                                       253

<210> SEQ ID NO 3
<211> LENGTH: 21
<212> TYPE: DNA
<213> ORGANISM: Prevotella

<400> SEQUENCE: 3
tacggaaggt ccgggcgtta t                                              21

<210> SEQ ID NO 4
<211> LENGTH: 21
<212> TYPE: DNA
<213> ORGANISM: Prevotella

<400> SEQUENCE: 4
agtgcagacg ttgagcgtct a                                              21

<210> SEQ ID NO 5
<211> LENGTH: 19
<212> TYPE: DNA
<213> ORGANISM: Prevotella

<400> SEQUENCE: 5
tacgtatggt gcaagcgtt                                                 19

<210> SEQ ID NO 6
<211> LENGTH: 21
<212> TYPE: DNA
<213> ORGANISM: Prevotella

<400> SEQUENCE: 6
gcagttcaga tgttgagcat c                                              21

<210> SEQ ID NO 7
<211> LENGTH: 252
<212> TYPE: DNA
<213> ORGANISM: Prevotella

<400> SEQUENCE: 7
tacggaaggt ccgggcgtta tccggattta ttgggtttaa agggagcgta ggccggagat    60
taagcgtgtt gtgaaatgta gacgctcaac gtctgcactg cagcgcgaac tggtttcctt    120
gagtacgcac aaagtgggcg gaattcgtgg tgtagcggtg aaatgcttag atatcacgaa    180
gaactccgat tgcgaaggca gctcactgga gcgcaactga cgctgaagct cgaaagtgcg    240
ggtatcgaac ag                                                        252
```

<210> SEQ ID NO 8
<211> LENGTH: 1494
<212> TYPE: DNA
<213> ORGANISM: Prevotella
<220> FEATURE:
<221> NAME/KEY: misc_feature
<222> LOCATION: (137)..(137)
<223> OTHER INFORMATION: y is c or t
<220> FEATURE:
<221> NAME/KEY: misc_feature
<222> LOCATION: (378)..(378)
<223> OTHER INFORMATION: r is a or g
<220> FEATURE:
<221> NAME/KEY: misc_feature
<222> LOCATION: (1029)..(1029)
<223> OTHER INFORMATION: y is c or t
<220> FEATURE:
<221> NAME/KEY: misc_feature
<222> LOCATION: (1129)..(1129)
<223> OTHER INFORMATION: y is c or t
<220> FEATURE:
<221> NAME/KEY: misc_feature
<222> LOCATION: (1254)..(1254)
<223> OTHER INFORMATION: y is c or t
<220> FEATURE:
<221> NAME/KEY: misc_feature
<222> LOCATION: (1255)..(1255)
<223> OTHER INFORMATION: s is g or c
<220> FEATURE:
<221> NAME/KEY: misc_feature
<222> LOCATION: (1257)..(1257)
<223> OTHER INFORMATION: y is c or t
<220> FEATURE:
<221> NAME/KEY: misc_feature
<222> LOCATION: (1258)..(1258)
<223> OTHER INFORMATION: y is c or t
<220> FEATURE:
<221> NAME/KEY: misc_feature
<222> LOCATION: (1260)..(1260)
<223> OTHER INFORMATION: y is c or t
<220> FEATURE:
<221> NAME/KEY: misc_feature
<222> LOCATION: (1266)..(1266)
<223> OTHER INFORMATION: s is g or c

<400> SEQUENCE: 8

| | | | | | |
|---|---|---|---|---|---|
| agagtttgat | cctggctcag | gatgaacgct | agctacaggc | ttaacacatg | caagtcgagg | 60 |
| ggaaacgaca | tcgaaagctt | gcttttgatg | ggcgtcgacc | ggcgcacggg | tgagtaacgc | 120 |
| gtatccaacc | tgcccaycac | ttggggataa | ccttgcgaaa | gtaagactaa | tacccaatga | 180 |
| tatctctaga | agacatctga | aagagattaa | agatttatcg | gtgatggatg | gggatgcgtc | 240 |
| tgattagctt | gttggcgggg | taacggccca | ccaaggcgac | gatcagtagg | ggttctgaga | 300 |
| ggaaggtccc | ccacattgga | actgagacac | ggtccaaact | cctacgggag | gcagcagtga | 360 |
| ggaatattgg | tcaatggrcg | agagcctgaa | ccagccaagt | agcgtgcagg | atgacggccc | 420 |
| tatgggttgt | aaactgcttt | tataagggaa | taaagtgagc | ctcgtgaggc | ttttttgcatg | 480 |
| taccttatga | ataaggaccg | gctaattccg | tgccagcagc | cgcggtaata | cggaaggtcc | 540 |
| gggcgttatc | cggatttatt | gggtttaaag | ggagcgtagg | ccggagatta | agcgtgttgt | 600 |
| gaaatgtaga | cgctcaacgt | ctgcactgca | gcgcgaactg | gtttccttga | gtacgcacaa | 660 |
| agtgggcgga | attcgtggtg | tagcggtgaa | atgcttagat | atcacgaaga | actccgattg | 720 |
| cgaaggcagc | tcactggagc | gcaactgacg | ctgaagctcg | aaagtgcggg | tatcgaacag | 780 |
| gattagatac | cctggtagtc | cgcacggtaa | acgatggatg | cccgctgttg | gtctgaacag | 840 |
| gtcagcggcc | aagcgaaagc | attaagcatc | ccacctgggg | agtacgccgg | caacggtgaa | 900 |

-continued

```
actcaaagga attgacgggg gcccgcacaa gcggaggaac atgtggttta attcgatgat    960
acgcgaggaa accttacccg ggcttgaatt gcagaggaag gatttggaga caatgacgcc   1020
cttcggggyc tctgtgaagg tgctgcatgg ttgtcgtcag ctcgtgccgt gaggtgtcgg   1080
cttaagtgcc ataacgagcg caacccctct ccttagttgc catcaggtya agctgggcac   1140
tctggggaca ctgccaccgt aaggtgtgag gaaggtgggg atgacgtcaa atcagcacgg   1200
cccttacgtc cggggctaca cacgtgttac aatggcaggt acagagagac ggtyscyygy   1260
aaagtsgatc aaatccttaa agcctgtctc agttcggact ggggtctgca acccgacccc   1320
acgaagctgg attcgctagt aatcgcgcat cagccatggc gcggtgaata cgttcccggg   1380
ccttgtacac accgcccgtc aagccatgaa agccggggc gcctaaagtc cgtgaccgta    1440
aggagcggcc tagggcgaaa ctggtaattg gggctaagtc gtaacaaggt aacc           1494
```

```
<210> SEQ ID NO 9
<211> LENGTH: 1491
<212> TYPE: DNA
<213> ORGANISM: Prevotella
<220> FEATURE:
<221> NAME/KEY: misc_feature
<222> LOCATION: (137)..(137)
<223> OTHER INFORMATION: y is c or t
<220> FEATURE:
<221> NAME/KEY: misc_feature
<222> LOCATION: (378)..(378)
<223> OTHER INFORMATION: r is a or g
<220> FEATURE:
<221> NAME/KEY: misc_feature
<222> LOCATION: (385)..(385)
<223> OTHER INFORMATION: y is c or t
<220> FEATURE:
<221> NAME/KEY: misc_feature
<222> LOCATION: (412)..(412)
<223> OTHER INFORMATION: w is a or t
<220> FEATURE:
<221> NAME/KEY: misc_feature
<222> LOCATION: (469)..(469)
<223> OTHER INFORMATION: r is a or g
<220> FEATURE:
<221> NAME/KEY: misc_feature
<222> LOCATION: (1126)..(1126)
<223> OTHER INFORMATION: y is c or t
<220> FEATURE:
<221> NAME/KEY: misc_feature
<222> LOCATION: (1128)..(1128)
<223> OTHER INFORMATION: w is a or t
<220> FEATURE:
<221> NAME/KEY: misc_feature
<222> LOCATION: (1195)..(1195)
<223> OTHER INFORMATION: y is c or t
<220> FEATURE:
<221> NAME/KEY: misc_feature
<222> LOCATION: (1251)..(1251)
<223> OTHER INFORMATION: y is c or t
<220> FEATURE:
<221> NAME/KEY: misc_feature
<222> LOCATION: (1252)..(1252)
<223> OTHER INFORMATION: s is g or c
<220> FEATURE:
<221> NAME/KEY: misc_feature
<222> LOCATION: (1253)..(1253)
<223> OTHER INFORMATION: y is c or t
<220> FEATURE:
<221> NAME/KEY: misc_feature
<222> LOCATION: (1254)..(1254)
<223> OTHER INFORMATION: w is a or t
<220> FEATURE:
<221> NAME/KEY: misc_feature
<222> LOCATION: (1255)..(1255)
<223> OTHER INFORMATION: y is c or t
<220> FEATURE:
<221> NAME/KEY: misc_feature
```

```
<222> LOCATION: (1257)..(1257)
<223> OTHER INFORMATION: y is c or t
<220> FEATURE:
<221> NAME/KEY: misc_feature
<222> LOCATION: (1260)..(1260)
<223> OTHER INFORMATION: r is a or g
<220> FEATURE:
<221> NAME/KEY: misc_feature
<222> LOCATION: (1261)..(1261)
<223> OTHER INFORMATION: w is a or t
<220> FEATURE:
<221> NAME/KEY: misc_feature
<222> LOCATION: (1263)..(1263)
<223> OTHER INFORMATION: s is g or c

<400> SEQUENCE: 9
agagtttgat cctggctcag gatgaacgct agctacaggc ttaacacatg caagtcgagg    60
ggaaacgaca tcgaaagctt gcttttgatg ggcgtcgacc ggcgcacggg tgagtaacgc   120
gtatccaacc tgcccaycac ttggggataa ccttgcgaaa gtaagactaa tacccaatga   180
tatctctaga agacatctga aagagattaa agatttatcg gtgatggatg gggatgcgtc   240
tgattagctt gttggcgggg taacggccca ccaaggcgac gatcagtagg ggttctgaga   300
ggaaggtccc ccacattgga actgagacac ggtccaaact cctacgggag gcagcagtga   360
ggaatattgg tcaatggrcg agagyctgaa ccagccaagt agcgtgcagg awgacggccc   420
tatgggttgt aaactgcttt tataagggaa taaagtgagc ctcgtgagrc ttttttgcatg   480
taccttatga ataaggaccg gctaattccg tgccagcagc cgcggtaata cggaaggtcc   540
gggcgttatc cggatttatt gggtttaaag ggagcgtagg ccggagatta agcgtgttgt   600
gaaatgtaga cgctcaacgt ctgcactgca gcgcgaactg gtttccttga gtacgcacaa   660
agtgggcgga attcgtggtg tagcggtgaa atgcttagat atcacgaaga actccgattg   720
cgaaggcagc tcactggagc gcaactgacg ctgaagctcg aaagtgcggg tatcgaacag   780
gattagatac cctggtagtc cgcacggtaa acgatggatg cccgctgttg gtctgaacag   840
gtcagcggcc aagcgaaagc attaagcatc ccacctgggg gagtacgccg gcaacggtga   900
aactcaaagg aattgacggg gcccgcacaa gcggaggaac atgtggttaa ttcgatgata   960
cgcgaggaac cttacccggg cttgaattgc agaggaagga ttggagacaa tgacgccctt  1020
cggggcctct gtgaaggtgc tgcatggttg tcgtcagctc gtgccgtgag gtgtcggctt  1080
aagtgccata acgagcgcaa cccctctcct tagttgccat caggtyawgc tgggcactct  1140
ggggacactg ccaccgtaag gtgtgaggaa ggtgggatg acgtcaaatc agcayggccc  1200
ttacgtccgg ggctacacac gtgttacaat ggcaggtaca gagagacggt ysywygyaar  1260
wtsgatcaaa tccttaaagc ctgtctcagt tcggactggg gtctgcaacc cgaccccacg  1320
aagctggatt cgctagtaat cgcgcatcag ccatggcgcg gtgaatacgt tcccgggcct  1380
tgtacacacc gcccgtcaag ccatgaaagc cgggggcgcc taaagtccgt gaccgtaagg  1440
agcggcctag ggcgaaactg gtaattgggg ctaagtcgta acaaggtaac c            1491

<210> SEQ ID NO 10
<211> LENGTH: 1493
<212> TYPE: DNA
<213> ORGANISM: Prevotella
<220> FEATURE:
<221> NAME/KEY: misc_feature
<222> LOCATION: (378)..(378)
<223> OTHER INFORMATION: r is a or g
<220> FEATURE:
<221> NAME/KEY: misc_feature
<222> LOCATION: (385)..(385)
```

```
<223> OTHER INFORMATION: y is c or t
<220> FEATURE:
<221> NAME/KEY: misc_feature
<222> LOCATION: (412)..(412)
<223> OTHER INFORMATION: w is a or t
<220> FEATURE:
<221> NAME/KEY: misc_feature
<222> LOCATION: (469)..(469)
<223> OTHER INFORMATION: r is a or g
<220> FEATURE:
<221> NAME/KEY: misc_feature
<222> LOCATION: (1028)..(1028)
<223> OTHER INFORMATION: y is c or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1253)..(1253)
<223> OTHER INFORMATION: y is c or t
<220> FEATURE:
<221> NAME/KEY: misc_feature
<222> LOCATION: (1254)..(1254)
<223> OTHER INFORMATION: s is g or c
<220> FEATURE:
<221> NAME/KEY: misc_feature
<222> LOCATION: (1255)..(1255)
<223> OTHER INFORMATION: y is c or t
<220> FEATURE:
<221> NAME/KEY: misc_feature
<222> LOCATION: (1256)..(1256)
<223> OTHER INFORMATION: w is a or t
<220> FEATURE:
<221> NAME/KEY: misc_feature
<222> LOCATION: (1259)..(1259)
<223> OTHER INFORMATION: y is c or t
<220> FEATURE:
<221> NAME/KEY: misc_feature
<222> LOCATION: (1262)..(1262)
<223> OTHER INFORMATION: r is a or g
<220> FEATURE:
<221> NAME/KEY: misc_feature
<222> LOCATION: (1263)..(1263)
<223> OTHER INFORMATION: w is a or t
<220> FEATURE:
<221> NAME/KEY: misc_feature
<222> LOCATION: (1265)..(1265)
<223> OTHER INFORMATION: s is g or c

<400> SEQUENCE: 10
agagtttgat cctggctcag gatgaacgct agctacaggc ttaacacatg caagtcgagg      60
ggaaacgaca tcgaaagctt gcttttgatg ggcgtcgacc ggcgcacggg tgagtaacgc     120
gtatccaacc tgcccaccac ttggggataa ccttgcgaaa gtaagactaa tacccaatga     180
tatctctaga agacatctga aagagattaa agatttatcg gtgatggatg gggatgcgtc     240
tgattagctt gttggcgggg taacggccca ccaaggcgac gatcagtagg ggttctgaga     300
ggaaggtccc ccacattgga actgagacac ggtccaaact cctacgggag gcagcagtga     360
ggaatattgg tcaatggrcg agagyctgaa ccagccaagt agcgtgcagg awgacggccc     420
tatgggttgt aaactgcttt tataagggaa taaagtgagc ctcgtgagrc tttttgcatg     480
taccttatga ataaggaccg gctaattccg tgccagcagc cgcggtaata cggaaggtcc     540
gggcgttatc cggatttatt gggtttaaag ggagcgtagg ccggagatta agcgtgttgt     600
gaaatgtaga cgctcaacgt ctgcactgca gcgcgaactg gtttccttga gtacgcacaa     660
agtgggcgga attcgtggtg tagcggtgaa atgcttagat atcacgaaga actccgattg     720
cgaaggcagc tcactggagc gcaactgacg ctgaagctcg aaagtgcggg tatcgaacag     780
gattagatac cctggtagtc cgcacggtaa acgatggatg cccgctgttg gtctgaacag     840
```

```
gtcagcggcc aagcgaaagc attaagcatc ccacctgggg agtacgccgg caacggtgaa    900
actcaaagga attgacgggg gcccgcacaa gcggaggaac atgtggttta attcgatgat    960
acgcgaggaa ccttacccgg gcttgaattg cagaggaagg atttggagac aatgacgccc   1020
ttcggggyct ctgtgaangt gctgcatggt tgtcgtcagc tcgtgccgtg aggtgtcggc   1080
ttaagtgcca taacgagcgc aaccectete cttagttgcc atcaggtcaa gctgggcact   1140
ctggggacac tgccaccgta aggtgtgagg aaggtgggga tgacgtcaaa tcagcacggc   1200
ccttacgtcc ggggctacac acgtgttaca atggcaggta cagagagacg gtysywtgya   1260
arwtsgatca aatccttaaa gcctgtctca gttcggactg gggtctgcaa cccgacccca   1320
cgaagctgga ttcgctagta atcgcgcatc agccatggcg cggtgaatac gttcccgggc   1380
cttgtacaca ccgcccgtca agccatgaaa gccggggcg cctaaagtcc gtgaccgtaa    1440
ggagcggcct agggcgaaac tggtaattgg ggctaagtcg taacaaggta acc          1493
```

<210> SEQ ID NO 11
<211> LENGTH: 1493
<212> TYPE: DNA
<213> ORGANISM: Prevotella
<220> FEATURE:
<221> NAME/KEY: misc_feature
<222> LOCATION: (137)..(137)
<223> OTHER INFORMATION: y is c or t
<220> FEATURE:
<221> NAME/KEY: misc_feature
<222> LOCATION: (378)..(378)
<223> OTHER INFORMATION: r is a or g
<220> FEATURE:
<221> NAME/KEY: misc_feature
<222> LOCATION: (385)..(385)
<223> OTHER INFORMATION: y is c or t
<220> FEATURE:
<221> NAME/KEY: misc_feature
<222> LOCATION: (469)..(469)
<223> OTHER INFORMATION: r is a or g
<220> FEATURE:
<221> NAME/KEY: misc_feature
<222> LOCATION: (1028)..(1028)
<223> OTHER INFORMATION: y is c or t
<220> FEATURE:
<221> NAME/KEY: misc_feature
<222> LOCATION: (1128)..(1128)
<223> OTHER INFORMATION: y is c or t
<220> FEATURE:
<221> NAME/KEY: misc_feature
<222> LOCATION: (1253)..(1253)
<223> OTHER INFORMATION: y is c or t
<220> FEATURE:
<221> NAME/KEY: misc_feature
<222> LOCATION: (1254)..(1254)
<223> OTHER INFORMATION: s is g or c
<220> FEATURE:
<221> NAME/KEY: misc_feature
<222> LOCATION: (1255)..(1255)
<223> OTHER INFORMATION: y is c or t
<220> FEATURE:
<221> NAME/KEY: misc_feature
<222> LOCATION: (1256)..(1256)
<223> OTHER INFORMATION: w is a or t
<220> FEATURE:
<221> NAME/KEY: misc_feature
<222> LOCATION: (1257)..(1257)
<223> OTHER INFORMATION: y is c or t
<220> FEATURE:
<221> NAME/KEY: misc_feature
<222> LOCATION: (1259)..(1259)
<223> OTHER INFORMATION: y is c or t
<220> FEATURE:
<221> NAME/KEY: misc_feature
<222> LOCATION: (1262)..(1262)

<223> OTHER INFORMATION: r is a or g
<220> FEATURE:
<221> NAME/KEY: misc_feature
<222> LOCATION: (1263)..(1263)
<223> OTHER INFORMATION: w is a or t
<220> FEATURE:
<221> NAME/KEY: misc_feature
<222> LOCATION: (1265)..(1265)
<223> OTHER INFORMATION: s is g or c

<400> SEQUENCE: 11

| | | | | | |
|---|---|---|---|---|---|
| agagtttgat | cctggctcag | gatgaacgct | agctacaggc | ttaacacatg | caagtcgagg 60 |
| ggaaacgaca | tcgaaagctt | gcttttgatg | ggcgtcgacc | ggcgcacggg | tgagtaacgc 120 |
| gtatccaacc | tgcccaycac | ttggggataa | ccttgcgaaa | gtaagactaa | tacccaatga 180 |
| tatctctaga | agacatctga | aagagattaa | agatttatcg | gtgatggatg | gggatgcgtc 240 |
| tgattagctt | gttggcgggg | taacggccca | ccaaggcgac | gatcagtagg | ggttctgaga 300 |
| ggaaggtccc | ccacattgga | actgagacac | ggtccaaact | cctacgggag | gcagcagtga 360 |
| ggaatattgg | tcaatggrcg | agagyctgaa | ccagccaagt | agcgtgcagg | atgacggccc 420 |
| tatgggttgt | aaactgcttt | tataagggaa | taaagtgagc | ctcgtgagrc | tttttgcatg 480 |
| taccttatga | ataaggaccg | gctaattccg | tgccagcagc | cgcggtaata | cggaaggtcc 540 |
| gggcgttatc | cggatttatt | gggtttaaag | ggagcgtagg | ccggagatta | agcgtgttgt 600 |
| gaaatgtaga | cgctcaacgt | ctgcactgca | gcgcgaactg | gtttccttga | gtacgcacaa 660 |
| agtgggcgga | attcgtggtg | tagcggtgaa | atgcttagat | atcacgaaga | actccgattg 720 |
| cgaaggcagc | tcactggagc | gcaactgacg | ctgaagctcg | aaagtgcggg | tatcgaacag 780 |
| gattagatac | cctggtagtc | cgcacggtaa | acgatggatg | cccgctgttg | gtctgaacag 840 |
| gtcagcggcc | aagcgaaagc | attaagcatc | ccacctgggg | agtacgccgg | caacggtgaa 900 |
| actcaaagga | attgacgggg | gcccgcacaa | gcggaggaac | atgtggttta | attcgatgat 960 |
| acgcgaggaa | ccttacccgg | gcttgaattg | cagaggaagg | atttggagac | aatgacgccc 1020 |
| ttcggggyct | ctgtgaaggt | gctgcatggt | tgtcgtcagc | tcgtgccgtg | aggtgtcggc 1080 |
| ttaagtgcca | taacgagcgc | aaccccctctc | cttagttgcc | atcaggtyaa | gctgggcact 1140 |
| ctggggacac | tgccaccgta | aggtgtgagg | aaggtgggga | tgacgtcaaa | tcagcacggc 1200 |
| ccttacgtcc | ggggctacac | acgtgttaca | atggcaggta | cagagagacg | gtysywygya 1260 |
| arwtsgatca | aatccttaaa | gcctgtctca | gttcggactg | gggtctgcaa | cccgacccca 1320 |
| cgaagctgga | ttcgctagta | atcgcgcatc | agccatggcg | cggtgaatac | gttcccgggc 1380 |
| cttgtacaca | ccgcccgtca | agccatgaaa | gccggggcg | cctaaagtcc | gtgaccgtaa 1440 |
| ggagcggcct | agggcgaaac | tggtaattgg | ggctaagtcg | taacaaggta | acc 1493 |

<210> SEQ ID NO 12
<211> LENGTH: 1493
<212> TYPE: DNA
<213> ORGANISM: Prevotella
<220> FEATURE:
<221> NAME/KEY: misc_feature
<222> LOCATION: (378)..(378)
<223> OTHER INFORMATION: r is a or g
<220> FEATURE:
<221> NAME/KEY: misc_feature
<222> LOCATION: (385)..(385)
<223> OTHER INFORMATION: y is c or t
<220> FEATURE:
<221> NAME/KEY: misc_feature
<222> LOCATION: (412)..(412)
<223> OTHER INFORMATION: w is a or t

```
<220> FEATURE:
<221> NAME/KEY: misc_feature
<222> LOCATION: (460)..(460)
<223> OTHER INFORMATION: y is c or t
<220> FEATURE:
<221> NAME/KEY: misc_feature
<222> LOCATION: (469)..(469)
<223> OTHER INFORMATION: r is a or g
<220> FEATURE:
<221> NAME/KEY: misc_feature
<222> LOCATION: (1128)..(1128)
<223> OTHER INFORMATION: y is c or t
<220> FEATURE:
<221> NAME/KEY: misc_feature
<222> LOCATION: (1253)..(1253)
<223> OTHER INFORMATION: y is c or t
<220> FEATURE:
<221> NAME/KEY: misc_feature
<222> LOCATION: (1254)..(1254)
<223> OTHER INFORMATION: s is g or c
<220> FEATURE:
<221> NAME/KEY: misc_feature
<222> LOCATION: (1255)..(1255)
<223> OTHER INFORMATION: y is c or t
<220> FEATURE:
<221> NAME/KEY: misc_feature
<222> LOCATION: (1256)..(1256)
<223> OTHER INFORMATION: w is a or t
<220> FEATURE:
<221> NAME/KEY: misc_feature
<222> LOCATION: (1259)..(1259)
<223> OTHER INFORMATION: y is c or t
<220> FEATURE:
<221> NAME/KEY: misc_feature
<222> LOCATION: (1262)..(1262)
<223> OTHER INFORMATION: r is a or g
<220> FEATURE:
<221> NAME/KEY: misc_feature
<222> LOCATION: (1263)..(1264)
<223> OTHER INFORMATION: w is a or t
<220> FEATURE:
<221> NAME/KEY: misc_feature
<222> LOCATION: (1265)..(1265)
<223> OTHER INFORMATION: s is g or c

<400> SEQUENCE: 12
agagtttgat cctggctcag gatgaacgct agctacaggc ttaacacatg caagtcgagg    60
ggaaacgaca tcgaaagctt gcttttgatg ggcgtcgacc ggcgcacggg tgagtaacgc   120
gtatccaacc tgcccaccac ttggggataa ccttgcgaaa gtaagactaa tacccaatga   180
tatctctaga agacatctga aagagattaa agatttatcg gtgatggatg gggatgcgtc   240
tgattagctt gttggcgggg taacggccca ccaaggcgac gatcagtagg ggttctgaga   300
ggaaggtccc ccacattgga actgagacac ggtccaaact cctacgggag gcagcagtga   360
ggaatattgg tcaatggrcg agagyctgaa ccagccaagt agcgtgcagg awgacggccc   420
tatgggttgt aaactgcttt tataagggaa taaagtgagy ctcgtgagrc tttttgcatg   480
taccttatga ataaggaccg gctaattccg tgccagcagc cgcggtaata cggaaggtcc   540
gggcgttatc cggatttatt gggtttaaag ggagcgtagg ccggagatta agcgtgttgt   600
gaaatgtaga cgctcaacgt ctgcactgca gcgcgaactg gtttccttga gtacgcacaa   660
agtgggcgga attcgtggtg tagcggtgaa atgcttagat atcacgaaga actccgattg   720
cgaaggcagc tcactggagc gcaactgacg ctgaagctcg aaagtgcggg tatcgaacag   780
gattagatac cctggtagtc cgcacggtaa acgatggatg cccgctgttg gtctgaacag   840
gtcagcggcc aagcgaaagc attaagcatc ccacctgggg agtacgccgg caacggtgaa   900
actcaaagga attgacgggg gcccgcacaa gcggaggaac atgtggttta attcgatgat   960
```

```
acgcgaggaa ccttacccgg gcttgaattg cagaggaagg atttggagac aatgacgccc    1020 ttcgggggcct ctgtgaaggt gctgcatggt tgtcgtcagc tcgtgccgtg aggtgtcggc   1080
ttaagtgcca taacgagcgc aaccsctctc cttagttgcc atcaggtyaa gctgggcact   1140
ctggggacac tgccaccgta aggtgtgagg aaggtgggga tgacgtcaaa tcagcacggc   1200
ccttacgtcc ggggctacac acgtgttaca atggcaggta cagagagacg gtysywtgya   1260
arwwsgatca aatccttaaa gcctgtctca gttcggactg gggtctgcaa cccgaccca    1320 cgaagctgga ttcgctagta atcgcgcatc agccatggcg cggtgaatac gttcccgggc   1380
cttgtacaca ccgcccgtca agccatgaaa gccgggggcg cctaaagtcc gtgaccgtaa   1440
ggagcggcct agggcgaaac tggtaattgg ggctaagtcg taacaaggta acc          1493
```

<210> SEQ ID NO 13
<211> LENGTH: 19
<212> TYPE: PRT
<213> ORGANISM: Artificial sequence
<220> FEATURE:
<223> OTHER INFORMATION: Synthetic primer

<400> SEQUENCE: 13

Gly Thr Gly Cys Cys Ala Gly Cys Met Gly Cys Cys Gly Cys Gly Gly
1               5                   10                  15

Thr Ala Ala

<210> SEQ ID NO 14
<211> LENGTH: 20
<212> TYPE: PRT
<213> ORGANISM: Artificial sequence
<220> FEATURE:
<223> OTHER INFORMATION: Synthetic primer

<400> SEQUENCE: 14

Gly Gly Ala Cys Thr Ala Cys His Val Gly Gly Gly Thr Trp Thr Cys
1               5                   10                  15

Thr Ala Ala Thr
            20